US012688905B2

(12) United States Patent
Sakarya et al.

(10) Patent No.: US 12,688,905 B2
(45) Date of Patent: Jul. 21, 2026

(54) METHOD AND SYSTEM OF CANCER DETECTION USING CpG-SNP CONTAMINATION MARKERS

(71) Applicant: GRAIL, LLC, Menlo Park, CA (US)

(72) Inventors: Onur Sakarya, Redwood City, CA (US); Christopher Chang, Palo Alto, CA (US); Ajinkya Kokate, Union City, CA (US); Samuel S. Gross, Sunnyvale, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 18/357,726

(22) Filed: Jul. 24, 2023

(65) Prior Publication Data

US 2024/0055073 A1     Feb. 15, 2024

Related U.S. Application Data

(60) Provisional application No. 63/392,056, filed on Jul. 25, 2022, provisional application No. 63/392,061, filed on Jul. 25, 2022.

(51) Int. Cl.
| | |
|---|---|
| *G16B 20/20* | (2019.01) |
| *G16B 40/00* | (2019.01) |
| *G16H 50/20* | (2018.01) |

(52) U.S. Cl.
CPC ............. *G16B 20/20* (2019.02); *G16B 40/00* (2019.02); *G16H 50/20* (2018.01)

(58) Field of Classification Search
None
See application file for complete search history.

(56) References Cited

FOREIGN PATENT DOCUMENTS

| | | |
|---|---|---|
| WO | WO 2016/115530 A1 | 7/2016 |
| WO | WO 2017/212428 A1 | 12/2017 |
| WO | WO 2019/010564 A1 | 1/2019 |
| WO | WO-2020232109 A1 * | 11/2020 ........... C12Q 1/6809 |
| WO | WO 2022/047082 A2 | 3/2022 |
| WO | WO 2022/061189 A1 | 3/2022 |

OTHER PUBLICATIONS

Liu et al. (Annals of Oncology, vol. 31, No. 6, Jun. 2020, pp. 745-759) (Year: 2020).*
Klein et al. (Annals of Oncology, vol. 32, No. 9, Sep. 2021, pp. 1167-1177) (Year: 2021).*
Whitty et al. (Sensitive detection of DNA Contamination in Tumor Samples via Microhaplotypes; BioRxiv, pp. 1-46; Preprint Pub. Date: Dec. 20, 2020; Pub. Date: Jan. 2022) (Year: 2022).*
PCT International Search Report and Written Opinion, PCT Application No. PCT/US2023/028484, Nov. 7, 2023, 12 pages.

* cited by examiner

*Primary Examiner* — Pablo S Whaley
(74) *Attorney, Agent, or Firm* — Fenwick & West LLP

(57) ABSTRACT

Methods and systems for detecting contaminated fragments in a biological sample for cancer classification are disclosed. The system identifies CpG-SNP contamination markers. The CpG-SNP contamination markers include at least one SNP that affects a CpG site. The CpG-SNP contamination markers may include additive CpG-SNP sites and/or subtractive CpG-SNP sites. Additive CpG-SNP sites include an SNP that creates a new CpG site. Subtractive CpG-SNP sites include an SNP that removes a preexisting CpG site. Hybrid sites may include additional sites. A multiple CpG-SNP contamination marker comprises two or more CpG-SNP sites. A CpG-SNP & indel contamination marker comprises at least one CpG-SNP site and an indel site. For a given sample, the system identifies contamination markers for which the sample is homozygous. The system determines fragments having a haplotype that is different from the homozygous haplotype of the sample to be contamination fragments.

18 Claims, 17 Drawing Sheets
Specification includes a Sequence Listing.

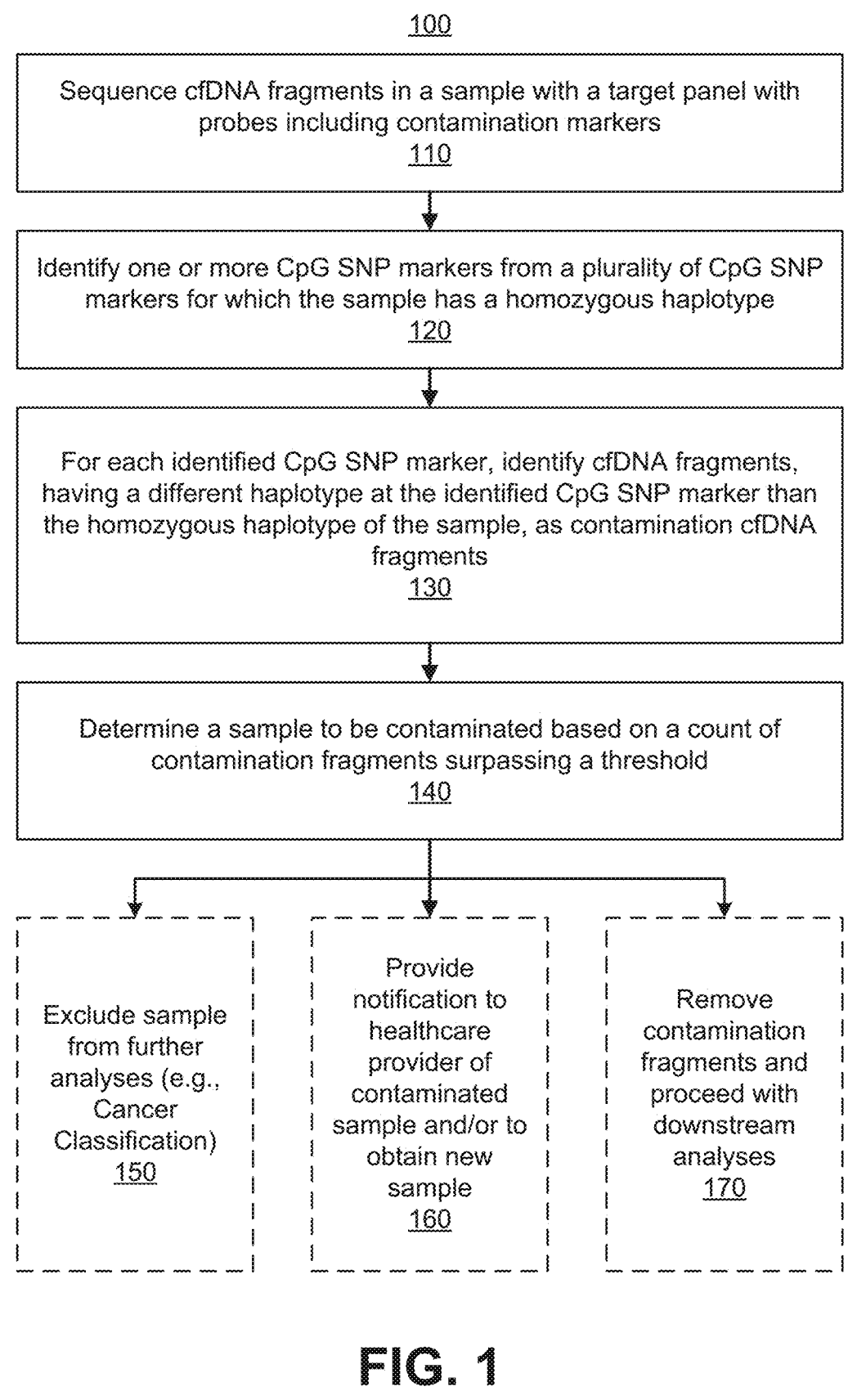

100

Sequence cfDNA fragments in a sample with a target panel with probes including contamination markers
110

↓

Identify one or more CpG SNP markers from a plurality of CpG SNP markers for which the sample has a homozygous haplotype
120

↓

For each identified CpG SNP marker, identify cfDNA fragments, having a different haplotype at the identified CpG SNP marker than the homozygous haplotype of the sample, as contamination cfDNA fragments
130

↓

Determine a sample to be contaminated based on a count of contamination fragments surpassing a threshold
140

Exclude sample from further analyses (e.g., Cancer Classification)
150

Provide notification to healthcare provider of contaminated sample and/or to obtain new sample
160

Remove contamination fragments and proceed with downstream analyses
170

FIG. 1

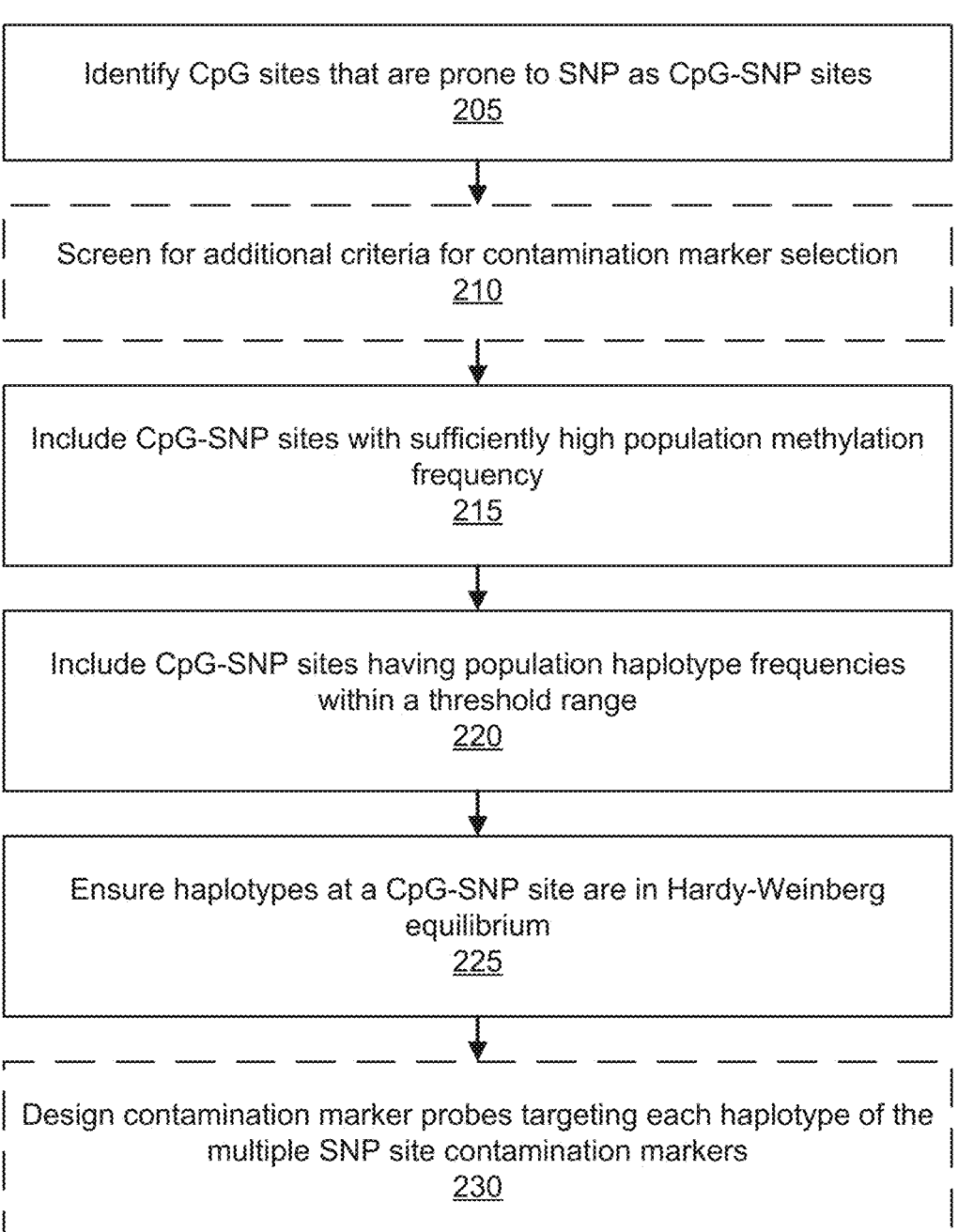

200

Identify CpG sites that are prone to SNP as CpG-SNP sites
205

Screen for additional criteria for contamination marker selection
210

Include CpG-SNP sites with sufficiently high population methylation frequency
215

Include CpG-SNP sites having population haplotype frequencies within a threshold range
220

Ensure haplotypes at a CpG-SNP site are in Hardy-Weinberg equilibrium
225

Design contamination marker probes targeting each haplotype of the multiple SNP site contamination markers
230

FIG. 2

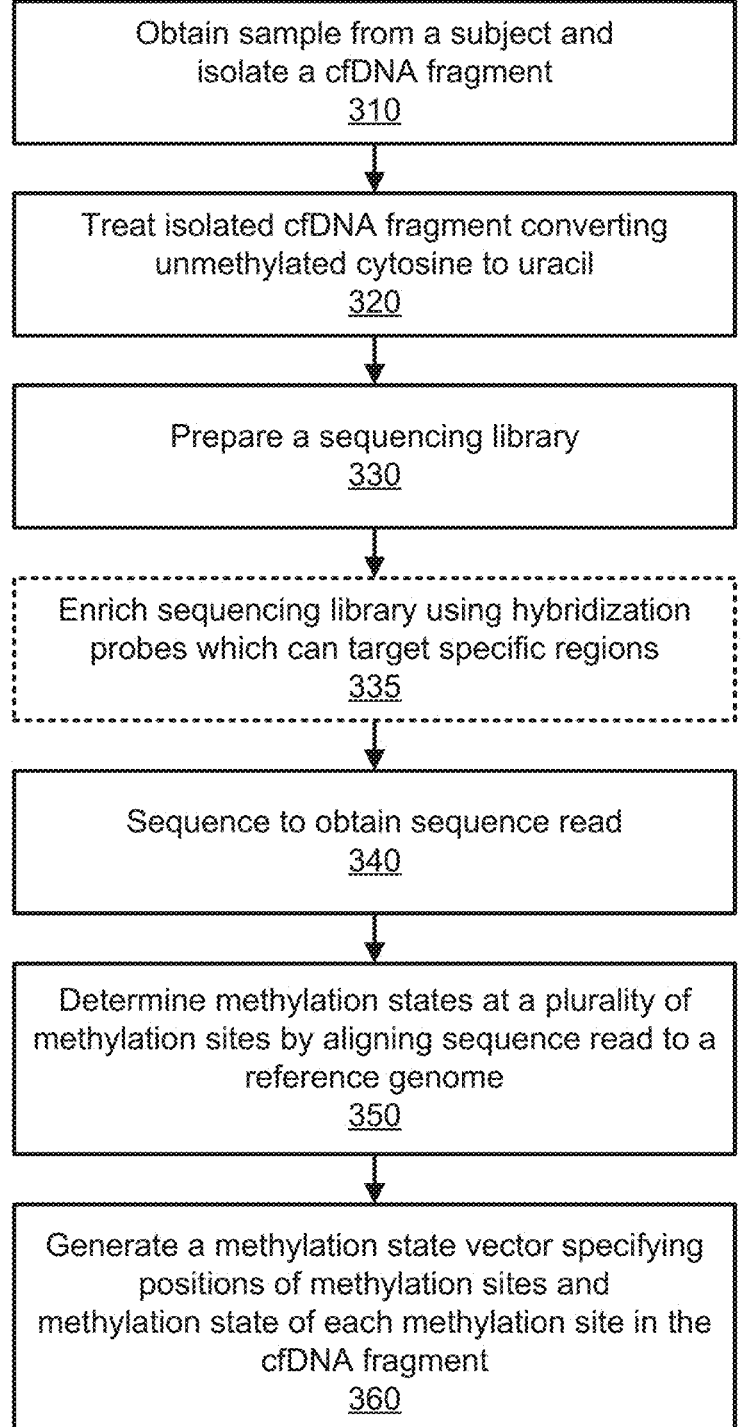

Generate methylation state vector from
cell-free (cf) DNA fragment in sample
300

Obtain sample from a subject and
isolate a cfDNA fragment
310

Treat isolated cfDNA fragment converting
unmethylated cytosine to uracil
320

Prepare a sequencing library
330

Enrich sequencing library using hybridization
probes which can target specific regions
335

Sequence to obtain sequence read
340

Determine methylation states at a plurality of
methylation sites by aligning sequence read to a
reference genome
350

Generate a methylation state vector specifying
positions of methylation sites and
methylation state of each methylation site in the
cfDNA fragment
360

FIG. 3A

Generate data structure for a control group
400

Generate set of methylation state vectors
for a control group
300

For each methylation state vector, subdivide into
strings of methylation sites
405

Tally strings for each position and methylation
state combination
410

Create data structure storing counts of all
possible strings from the control group
415

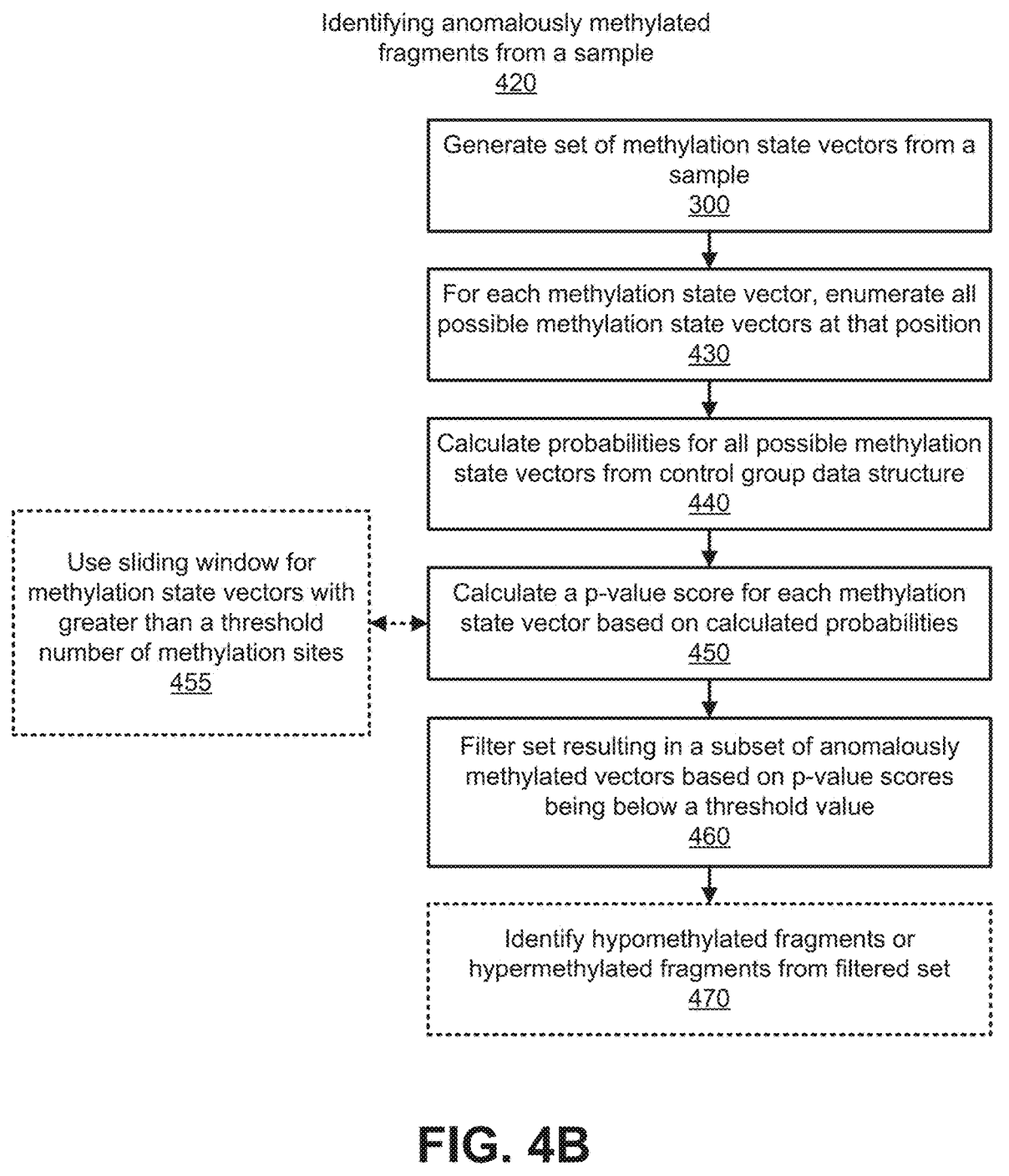

Identifying anomalously methylated
fragments from a sample
420

Generate set of methylation state vectors from a
sample
300

For each methylation state vector, enumerate all
possible methylation state vectors at that position
430

Calculate probabilities for all possible methylation
state vectors from control group data structure
440

Use sliding window for
methylation state vectors with
greater than a threshold
number of methylation sites
455

Calculate a p-value score for each methylation
state vector based on calculated probabilities
450

Filter set resulting in a subset of anomalously
methylated vectors based on p-value scores
being below a threshold value
460

Identify hypomethylated fragments or
hypermethylated fragments from filtered set
470

FIG. 4B

Training of Cancer Classifier
500

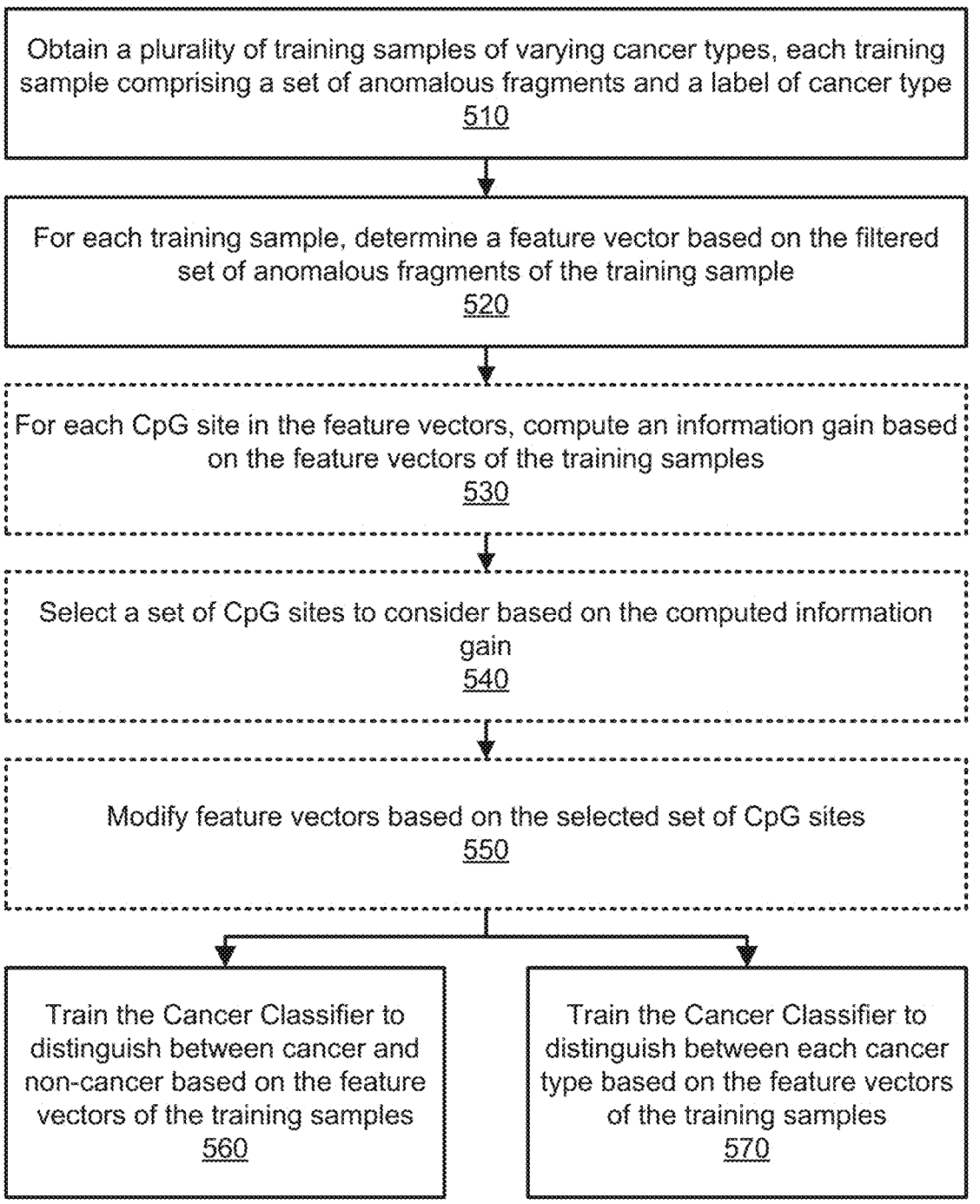

Obtain a plurality of training samples of varying cancer types, each training sample comprising a set of anomalous fragments and a label of cancer type
510

For each training sample, determine a feature vector based on the filtered set of anomalous fragments of the training sample
520

For each CpG site in the feature vectors, compute an information gain based on the feature vectors of the training samples
530

Select a set of CpG sites to consider based on the computed information gain
540

Modify feature vectors based on the selected set of CpG sites
550

Train the Cancer Classifier to distinguish between cancer and non-cancer based on the feature vectors of the training samples
560

Train the Cancer Classifier to distinguish between each cancer type based on the feature vectors of the training samples
570

FIG. 5A

Sequence
Reads

Sample C
810
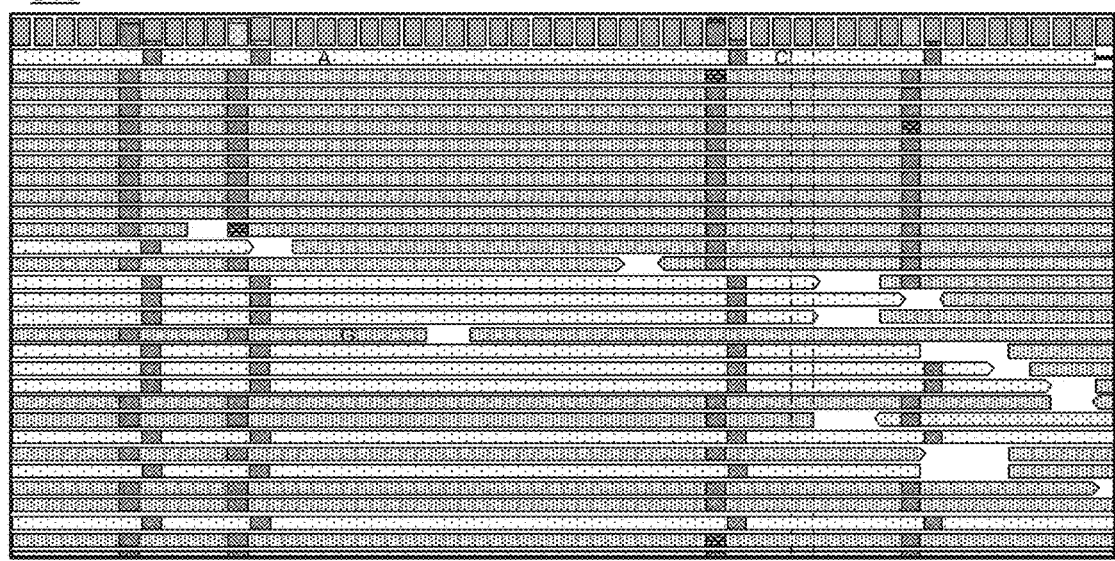
Sample D
820
⊠ Methylated
⊞ Unmethylated
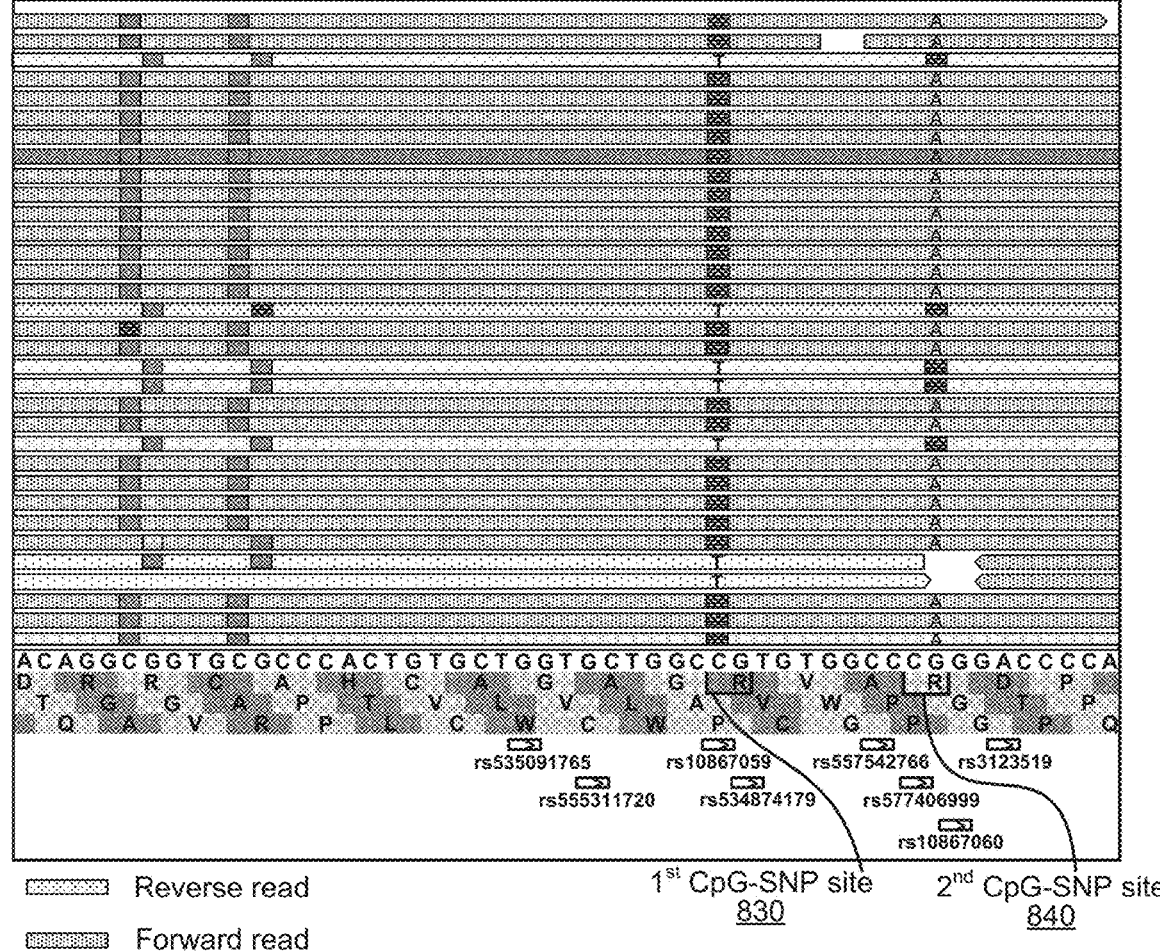
▭ Reverse read
▭ Forward read
1ˢᵗ CpG-SNP site
830
2ⁿᵈ CpG-SNP site
840
FIG. 8A

SEQUENCE LISTING

```
Sequence total quantity: 16
SEQ ID NO: 1              moltype = DNA   length = 21
FEATURE                   Location/Qualifiers
source                    1..21
                          mol_type = other DNA
                          organism = synthetic construct
SEQUENCE: 1
acgttttttt tttttttttac g                                     21

SEQ ID NO: 2              moltype = DNA   length = 29
FEATURE                   Location/Qualifiers
source                    1..29
                          mol_type = other DNA
                          organism = synthetic construct
SEQUENCE: 2
acgtcatcat catcatcatc atcatacgt                              29

SEQ ID NO: 3              moltype = DNA   length = 11
FEATURE                   Location/Qualifiers
source                    1..11
                          mol_type = other DNA
                          organism = synthetic construct
modified_base             10
                          mod_base = OTHER
                          note = methylated nucleotide
SEQUENCE: 3
tgcccagaac g                                                 11

SEQ ID NO: 4              moltype = DNA   length = 41
FEATURE                   Location/Qualifiers
source                    1..41
                          mol_type = genomic DNA
                          organism = Homo sapiens
SEQUENCE: 4
gcatgtgctg agggaagacc ggcaggactt gagtagttag a                41

SEQ ID NO: 5              moltype = DNA   length = 51
FEATURE                   Location/Qualifiers
source                    1..51
                          mol_type = genomic DNA
                          organism = Homo sapiens
SEQUENCE: 5
acaggcggtg cgcccactgt gctggtgctg gccgtgtggc ccgggacccc a     51

SEQ ID NO: 6              moltype = AA    length = 17
FEATURE                   Location/Qualifiers
source                    1..17
                          mol_type = protein
                          organism = Homo sapiens
```

-continued

```
SEQUENCE: 6
DRRCAHCAGA GRVARDP                                                    17

SEQ ID NO: 7            moltype = AA   length = 17
FEATURE                 Location/Qualifiers
source                  1..17
                        mol_type = protein
                        organism = Homo sapiens
SEQUENCE: 7
TGGAPTVLVL AVWPGTP                                                    17

SEQ ID NO: 8            moltype = AA   length = 17
FEATURE                 Location/Qualifiers
source                  1..17
                        mol_type = protein
                        organism = Homo sapiens
SEQUENCE: 8
QAVRPLCWCW PCGPGPQ                                                    17

SEQ ID NO: 9            moltype = DNA   length = 78
FEATURE                 Location/Qualifiers
source                  1..78
                        mol_type = genomic DNA
                        organism = Homo sapiens
SEQUENCE: 9
ggcggtgcgc ccactgtgct ggtgctggcc gtgtggcccg gaccccaga gggaggcagt   60
ggtcaagtgg cgctggat                                                  78

SEQ ID NO: 10           moltype = DNA   length = 49
FEATURE                 Location/Qualifiers
source                  1..49
                        mol_type = genomic DNA
                        organism = Homo sapiens
SEQUENCE: 10
tgcccagaac tgtggtttcc tgcagggcag gccccgcaag ggccgggcc                49

SEQ ID NO: 11           moltype = DNA   length = 72
FEATURE                 Location/Qualifiers
source                  1..72
                        mol_type = genomic DNA
                        organism = Homo sapiens
SEQUENCE: 11
acaggcggtg cgcccactgt gctggtgctg gccgtgtggc ccgggacccc agagggaggc   60
agtggtcaag tg                                                        72

SEQ ID NO: 12           moltype = AA   length = 24
FEATURE                 Location/Qualifiers
source                  1..24
                        mol_type = protein
                        organism = Homo sapiens
SEQUENCE: 12
DRRCAHCACA GRVARDPRCR QWSS                                            24

SEQ ID NO: 13           moltype = AA   length = 24
FEATURE                 Location/Qualifiers
source                  1..24
                        mol_type = protein
                        organism = Homo sapiens
SEQUENCE: 13
TGGAPTVLVL AVWPGTPCCC SGQV                                            24

SEQ ID NO: 14           moltype = AA   length = 24
FEATURE                 Location/Qualifiers
source                  1..24
                        mol_type = protein
                        organism = Homo sapiens
SEQUENCE: 14
QAVRPLCWCW PCCPCPQRLA VVRR                                            24

SEQ ID NO: 15           moltype = DNA   length = 79
FEATURE                 Location/Qualifiers
source                  1..79
                        mol_type = genomic DNA
                        organism = Homo sapiens
SEQUENCE: 15
aggatagtca caccaaggtg agtccagaac tgcccagaac tgtggtttcc tgcagggcag   60
gccccgcaag ggccgggcc                                                 79

SEQ ID NO: 16           moltype = DNA   length = 11
```

-continued

| FEATURE | Location/Qualifiers |
| --- | --- |
| source | 1..11 |
| | mol_type = genomic DNA |
| | organism = Homo sapiens |

SEQUENCE: 16 acaccggcat g                                                                                                    11

METHOD AND SYSTEM OF CANCER DETECTION USING CpG-SNP CONTAMINATION MARKERS

CROSS-REFERENCE TO RELATED APPLICATIONS

This application claims the benefit of U.S. Provisional Patent Application No. 63/392,056 filed on Jul. 25, 2022, and U.S. Provisional Patent Application No. 63/392,061, filed on Jul. 25, 2022, all of which are incorporated by reference herein in their entirety.

BACKGROUND

Sequence Listing

The instant application contains a Sequence Listing which has been submitted electronically in XML format and is hereby incorporated by reference in its entirety. Said XML copy, created on Sep. 6, 2023, is named 56088US_CRF_sequencelisting.xml and is 15,832 bytes in size.

FIELD OF ART

Deoxyribonucleic acid (DNA) methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free (cf) DNA. However, there remains a need in the art for improved methods of contamination detection of cfDNA fragments not derived from the individual of the sample. Contamination fragments can severely hinder both the training of diagnostic models and the detection of disease in a test sample.

The present disclosure is directed to addressing the above-referenced challenge. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

Early detection of a disease state (such as cancer) in subjects is important as it allows for earlier treatment and therefore a greater chance for survival. Sequencing of DNA fragments in cell-free (cf) DNA samples can be used to identify features that can be used for disease classification. For example, in cancer assessment, cell-free DNA based features (such as presence or absence of a somatic variant, methylation status, or other genetic aberrations) from a blood sample can provide insight into whether a subject may have cancer, and further insight on what type of cancer the subject may have. Towards that end, this description includes systems and methods for analyzing cell-free DNA (cfDNA) sequencing data for determining a subject's likelihood of having a disease.

The present disclosure addresses the problems identified above by providing improved systems and methods for sample contamination detection of contaminated fragments for cancer classification. The system utilizes CpG single nucleotide polymorphism (SNP) contamination markers. Each CpG-SNP contamination marker targets at least one CpG-SNP site comprising a SNP affecting a CpG site. Additive CpG-SNP sites include a SNP that creates a new CpG site. Subtractive CpG-SNP sites include a SNP that removes a preexisting CpG site. Other CpG-SNP contamination markers target at least one CpG-SNP site and another mutation site (e.g., a second CpG-SNP site in a threshold distance, and/or an indel site in a threshold distance). As these particular contamination markers involve both a SNP and an affected CpG site, the combined error rate is a product of the bisulfite conversion error rate and the SNP error rate, resulting in a very low combined error rate.

In one aspect of disclosure, a method is disclosed for predicting a presence of cancer in a test sample, the method comprising: obtaining sequence reads derived from a plurality of cell-free DNA (cfDNA) fragments in the test sample; identifying, based on the sequence reads, one or more CpG single nucleotide polymorphism (CpG-SNP) markers from a plurality of CpG-SNP markers for which the test sample has a homozygous haplotype, each CpG-SNP marker comprising a SNP affecting a CpG site; for each of the identified one or more CpG-SNP markers for which the test sample has a homozygous haplotype, determining whether the sequence reads for the cfDNA fragments have a different haplotype at the identified CpG-SNP marker than the homozygous haplotype of the test sample, wherein cfDNA fragments having a different haplotype at the identified CpG-SNP marker than the homozygous haplotype of the test sample are labeled as contamination cfDNA fragments; determining whether the test sample is contaminated based on presence of a number of contamination cfDNA fragments being above a threshold number; and in response to determining that the test sample is not contaminated, generating a cancer prediction for the test sample based on the sequence reads for the cfDNA fragments.

The method, further comprising: in response to determining that the test sample is contaminated, withholding generation of a cancer prediction for the test sample based on the sequence reads for the cfDNA fragments.

The method, wherein generating the cancer prediction for the test sample based on the sequence reads for the cfDNA fragments comprises: generating a test feature vector based on the sequence reads; and inputting the test feature vector into a classification model to generate the cancer prediction for the test sample.

The method, wherein a first CpG-SNP marker is an additive CpG-SNP site, wherein the SNP at the first CpG SNP marker creates a new CpG site.

The method, wherein the first CpG SNP marker is one of: a thymine-cytosine polymorphism in a thymine-guanine dinucleotide; an adenine-cytosine polymorphism in an adenine-guanine dinucleotide; a guanine-cytosine polymorphism in a guanine-guanine dinucleotide; a thymine-guanine polymorphism in a cytosine-thymine dinucleotide;

an adenine-guanine polymorphism in a cytosine-adenine dinucleotide; and a cytosine-guanine polymorphism in a cytosine-cytosine dinucleotide.

The method, wherein a first CpG-SNP marker is a subtractive CpG-SNP site, wherein the SNP at the first CpG SNP marker removes a preexisting CpG site.

The method, wherein the first CpG SNP marker is one of: a cytosine-thymine polymorphism in a cytosine-guanine dinucleotide; a cytosine-adenine polymorphism in a cytosine-guanine dinucleotide; a cytosine-guanine polymorphism in a cytosine-guanine dinucleotide; a guanine-thymine polymorphism in a cytosine-guanine dinucleotide; a guanine-adenine polymorphism in a cytosine-guanine dinucleotide; and a guanine-cytosine polymorphism in a cytosine-guanine dinucleotide.

The method, wherein a given CpG-SNP marker has a population methylation frequency above a threshold frequency.

The method, wherein the threshold frequency is selected from the range of 70%-100%.

The method, wherein each CpG-SNP marker has population haplotype frequencies within the range of 45%-55%.

The method, wherein the haplotypes of each CpG-SNP marker are in Hardy-Weinberg equilibrium.

The method, wherein a given CpG-SNP marker further comprises a second SNP affecting a second CpG site.

The method, wherein the second CpG site and the first CpG site of the given CpG-SNP marker are within a threshold distance.

The method, wherein the threshold distance is selected from the range of 8 bp to 30 bp.

The method, wherein the first SNP removes the first CpG site and the second SNP removes the second CpG site.

The method, wherein the first SNP removes the first CpG site and the second SNP creates the second CpG site.

The method, wherein the first SNP creates the first CpG site and the second SNP creates the second CpG site.

The method, wherein the given CpG SNP marker has population haplotype frequencies within the range of 45%-55%.

The method, wherein the haplotypes of the given CpG SNP marker are in Hardy-Weinberg equilibrium.

The method, wherein the given SNP CpG marker further comprises an insertion sequence within a threshold distance from the CpG site and the second CpG site.

The method, wherein the threshold distance is selected from 100 bp to 5 kbp.

The method, wherein the insertion sequence is of a threshold length.

The method, wherein the threshold length is selected from 5 bp to 30 bp.

The method, wherein the insertion sequence affects a third CpG site.

The method, wherein the third CpG site has a population methylation frequency above a threshold frequency.

The method, wherein the given CpG-SNP marker has population haplotype frequencies within the range of 45%-55%.

The method, wherein the haplotypes of the given CpG-SNP marker are in Hardy-Weinberg equilibrium.

The method, wherein each contamination marker includes a probe designed to target each haplotype of the contamination marker.

The method, wherein the cancer prediction is a binary prediction between cancer and non-cancer.

The method, wherein the cancer prediction is a multiclass cancer prediction between a plurality of cancer types.

The method, wherein each of the cfDNA fragments is an anomalous fragment, the method of claim 1 further comprising: filtering an initial set of cfDNA fragments of the test sample with p-value filtering to generate the set of anomalous fragments, the filtering comprising removing fragments from the initial set having below a threshold p-value with respect to other fragments to produce the set of anomalous fragments.

In another aspect, a method is disclosed for predicting a presence of contamination in a test sample, the method comprising: obtaining sequence reads derived from a plurality of cell-free DNA (cfDNA) fragments in the test sample; identifying, based on the sequence reads, one or more CpG single nucleotide polymorphism (SNP) markers from a plurality of CpG SNP markers for which the test sample has a homozygous haplotype, each CpG SNP marker comprising a SNP at a CpG site; for each of the identified one or more CpG SNP markers for which the test sample has a homozygous haplotype, determining whether the sequence reads for the cfDNA fragments have a different haplotype at the identified CpG SNP marker than the homozygous haplotype of the test sample, wherein cfDNA fragments having a different haplotype at the identified CpG SNP marker than the homozygous haplotype of the test sample are labeled as contamination cfDNA fragments; determining whether the test sample is contaminated based on presence of a number of contamination cfDNA fragments being above a threshold number; and in response to determining that the test sample is contaminated, generating a notification indicating that the test sample is contaminated.

In another aspect, a method is disclosed for predicting a presence of cancer in a test sample, the method comprising: obtaining sequence reads derived from a plurality of cell-free DNA (cfDNA) fragments in the test sample; identifying, based on the sequence reads, one or more CpG single nucleotide polymorphism (SNP) markers from a plurality of CpG SNP markers for which the test sample has a homozygous haplotype, each CpG SNP marker comprising a SNP at a CpG site; for each of the identified one or more CpG SNP markers for which the test sample has a homozygous haplotype, filtering the cfDNA fragments by removing one or more cfDNA fragments having a different haplotype at the identified CpG SNP marker than the homozygous haplotype of the test sample; generating a test feature vector based on the sequence reads of the filtered set of cfDNA fragments; and inputting the test feature vector into a classification model to generate a cancer prediction for the test sample.

In another aspect, a method is disclosed for training a cancer classification model, the method comprising: obtaining a plurality of training samples including a first training sample, each training sample comprising a plurality of cell-free DNA (cfDNA) fragments; for each training sample, obtaining sequence reads derived from the cfDNA fragments in the training sample; for the first training sample, identifying, based on the sequence reads of the first training sample, one or more CpG single nucleotide polymorphism (SNP) markers from a plurality of CpG SNP markers for which the first training sample has a homozygous haplotype, each CpG SNP marker comprising a SNP at a CpG site; for each of the identified one or more CpG SNP markers for which the first training sample has a homozygous haplotype, determining whether the sequence reads for the cfDNA fragments of the first training sample have a different haplotype at the identified CpG SNP marker than the homozygous haplotype of the first training sample, wherein cfDNA fragments having a different haplotype at the identified CpG SNP marker than the homozygous haplotype of the first training sample are labeled as contamination cfDNA fragments; determining whether the first training sample is contaminated based on presence of a number of contamination cfDNA fragments being above a threshold number; and in response to determining that the first training sample is contaminated, removing the first training sample from the plurality of training samples, wherein the plurality of training samples excluding the first training sample are used to train the cancer classification model to generate a cancer prediction for a test sample.

In another aspect, a system is disclosed comprising: a computer processor; and a non-transitory computer-readable storing instructions that, when executed by the computer processor, cause the computer processor to perform any of the preceding methods.

BRIEF DESCRIPTION OF DRAWINGS

FIG. 1 is an exemplary flowchart describing a process of contamination detection in a sample, according to one or more embodiments.

FIG. 2 is an exemplary flowchart describing a process of identifying CpG-SNP sites for use as contamination markers in contamination detection, according to one or more embodiments.

FIG. 3A is an exemplary flowchart describing a process of sequencing a fragment of cell-free (cf) DNA to obtain a methylation state vector, according to one or more embodiments.

FIGS. 4A & 4B illustrate exemplary flowcharts describing a process of determining anomalously methylated fragments from a sample, according to one or more embodiments.

FIG. 5A is an exemplary flowchart describing a process of training a cancer classifier, according to one or more embodiments.

FIG. 8A illustrates a hybrid site as a double CpG-SNP site with Sample C as homozygous absent two SNPs and Sample D as homozygous present two SNPs, according to example results. Figure discloses SEQ ID NOS 5-8.

FIG. 9A discloses SEQ 11-14. FIG. 9B discloses SEQ ID NO: 10. FIG. 9C discloses SEQ ID NOS 11-14. FIG. 9D discloses SEQ ID NO: 10.

FIG. 9E discloses SEQ ID NO: 15.

Figure 3B:
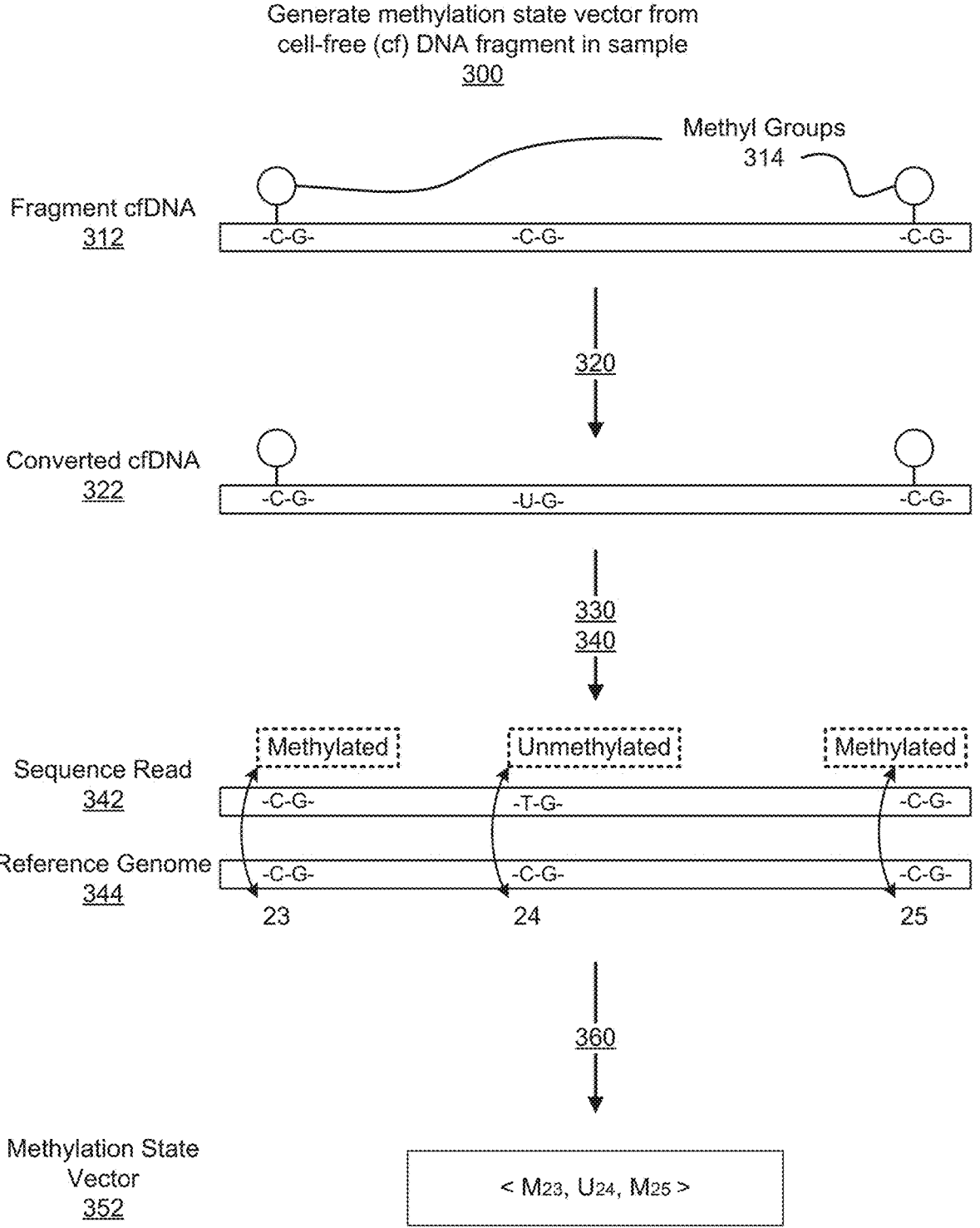
FIG. 3B is an exemplary illustration of the process of FIG. 3A of sequencing a fragment of cell-free (cf) DNA to obtain a methylation state vector, according to one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

I. Overview

Cancer detection based on the analysis of DNA fragments is enabled by next-generation sequencing ("NGS") techniques. NGS, broadly, is group of technologies that allows for high throughput sequencing of genetic material. As discussed in greater detail herein, NGS largely consists of sample preparation, DNA sequencing, and data analysis. Sample preparation is the laboratory methods necessary to prepare DNA fragments for sequencing, sequencing is the process of reading the ordered nucleotides in the samples, and data analysis is processing and analyzing the genetic information in the sequencing data to identify cancer presence.

While these steps of NGS may help enable early cancer detection, they also introduce their own complex, detrimental problems to cancer detection and, therefore, any improvements to sample preparation, DNA sequencing, and/or data analysis results in an improvement to cancer detection technologies.

To illustrate, as an example, problems introduced in sample preparation include DNA sample quality, sample contamination, fragmentation bias, and accurate indexing, and remedying those problems would yield better genetic data for cancer detection. Similarly, problems introduced in sequencing include, for example, errors in accurate transcribing of fragments (e.g., reading an "A" instead of a "C", etc.), incorrect or difficult fragment assembly and overlap, disparate coverage uniformity, sequencing depth vs. cost vs. specificity, and insufficient sequencing length. Again, remedying any of these problems would yield improved genetic data for cancer detection.

The problems in data analysis are possibly the most daunting and complex. The introduced challenges stem from the vast amounts of data created by NGS sequencing techniques. The created genetic datasets are typically on the order of terabytes, and effectively analyzing that amount of data is both procedurally and computationally demanding. For instance, analyzing NGS sequencing involves several baseline processing steps such as, e.g., aligning reads to one another, aligning and mapping reads to a reference genome, identifying and calling variant genes, identifying and calling abnormally methylated genes, generating functional annotations, etc. Performing any of these processes on terabytes of genetic data is computationally expensive for even the most powerful of computer architectures, and completely impossible for a normal human mind. Additionally, with the genetic sequencing data derived from the error-prone processes of sample preparation and sequence reading, large portions of the resulting genetic data may be low-quality or unusable for cancer identification. For example, large amounts of the genetic data may include contaminated samples, transcription errors, mismatched regions, overrepresented regions, etc. and may be unsuitable for high accuracy cancer detection. Identifying and accounting for low quality genetic data across the vast amount of genetic data obtained from NGS sequencing is also procedurally and computationally rigorous to accomplish and is also not practically performable by a human mind. Overall, any process created that leads to more efficient processing of large array sequencing data would be an improvement to cancer detection using NGS sequencing.

One of the problems in creating and appropriately applying a cancer detection model is, as described above, the vast amount of sequencing data to which the model may be applied. For instance, consider a machine-learned model that is configured to identify cancer based on anomaly scores for CpG sites at various genomic locations. The model, for instance, identifies cancer because of an anomaly score of a first CpG site indicates cancer, an anomaly score of a second CpG site indicates cancer, and an anomaly score of a third CpG site does not indicate cancer, etc. Given the traditional sample size of fragment-based cancer detection, this generally leads to tens of thousands of genomic sites indicative of cancer. For the machine learned model to process that amount of data is computationally expensive.

One technical problem that arises in the field of early cancer detection and cfDNA processing is that contamination of samples may occur with foreign fragments from another individual or organism in the process of, for example, transporting, obtaining, preparing the samples for sequence analysis. Since training data for the cancer detection model used to train the parameters of the cancer detection model may be obtained from samples of cfDNA fragments and the identification of at least one SNP at CpG sites in the sequence, contamination of samples for which data would be included in the training data of the machine-learned cancer detection model can lead to deteriorated accuracy if the model was trained using the contaminated samples. Moreover, even during inference or deployment using the cancer detection model, the detection of contamination is important because if a test sample for a subject is contaminated, the inference results of whether the subject has cancer or not may be inaccurate.

Therefore, as described herein, a method for detecting contaminated cfDNA fragments is disclosed, which allows an analytics system to determine whether a sample has been contaminated using contamination marker probes, determining whether the sequence reads for the cfDNA fragments have a different haplotype at the identified CpG-SNP marker than the homozygous haplotype of the test sample, and analyzing the number of contamination cfDNA fragments that have different haplotypes to determine whether the sample is contaminated or not.

By doing so, processes such as filtering the contaminated cfDNA fragments from the sample or withholding the sample from being included in the training or inference process can be performed such that more accurate data on SNP at CpG sites can be obtained. This allows a technical improvement in the training the machine-learned cancer detection model or the inference process of using a trained model to determine cancer detections for a subject. This is a practical application to the field of early cancer detection and training and inference using machine-learned cancer detection models.

I.A. Overview of Methylation

In accordance with the present description, cfDNA fragments from an individual are treated, for example by converting unmethylated cytosines to uracils, sequenced and the sequence reads compared to a reference genome to identify the methylation states at specific CpG sites within the DNA fragments. Each CpG site may be methylated or unmethylated. Identification of anomalously methylated fragments, in comparison to healthy individuals, may provide insight into a subject's cancer status. As is well known in the art, DNA methylation anomalies (compared to healthy controls) can cause different effects, which may contribute to cancer. Various challenges arise in the identification of anomalously methylated cfDNA fragments. First off, determining a DNA fragment to be anomalously methylated can hold weight in comparison with a group of control individuals, such that if the control group is small in number, the determination loses confidence due to statistical variability within the smaller size of the control group. Additionally, among a group of control individuals, methylation status can vary which can be difficult to account for when determining a subject's DNA fragments to be anomalously methylated. On another note, methylation of a cytosine at a CpG site can causally influence methylation at a subsequent CpG site. To encapsulate this dependency can be another challenge in itself.

Methylation can typically occur in deoxyribonucleic acid (DNA) when a hydrogen atom on the pyrimidine ring of a cytosine base is converted to a methyl group, forming 5-methylcytosine. In particular, methylation can occur at dinucleotides of cytosine and guanine referred to herein as "CpG sites". In other instances, methylation may occur at a cytosine not part of a CpG site or at another nucleotide that is not cytosine; however, these are rarer occurrences. In this present disclosure, methylation is discussed in reference to CpG sites for the sake of clarity. Anomalous DNA methylation can be identified as hypermethylation or hypomethylation, both of which may be indicative of cancer status. Throughout this disclosure, hypermethylation and hypomethylation can be characterized for a DNA fragment, if the DNA fragment comprises more than a threshold number of CpG sites with more than a threshold percentage of those CpG sites being methylated or unmethylated.

The principles described herein can be equally applicable for the detection of methylation in a non-CpG context, including non-cytosine methylation. In such embodiments, the wet laboratory assay used to detect methylation may vary from those described herein. Further, the methylation state vectors discussed herein may contain elements that are generally sites where methylation has or has not occurred (even if those sites are not CpG sites specifically). With that substitution, the remainder of the processes described herein can be the same, and consequently the inventive concepts described herein can be applicable to those other forms of methylation.

I.B. Definitions

The term "cell free nucleic acid" or "cfNA" refers to nucleic acid fragments that circulate in an individual's body (e.g., blood) and originate from one or more healthy cells and/or from one or more unhealthy cells (e.g., cancer cells). The term "cell free DNA," or "cfDNA" refers to deoxyribonucleic acid fragments that circulate in an individual's body (e.g., blood). Additionally, cfNAs or cfDNA in an individual's body may come from other non-human sources.

The term "genomic nucleic acid," "genomic DNA," or "gDNA" refers to nucleic acid molecules or deoxyribonucleic acid molecules obtained from one or more cells. In various embodiments, gDNA can be extracted from healthy cells (e.g., non-tumor cells) or from tumor cells (e.g., a biopsy sample). In some embodiments, gDNA can be extracted from a cell derived from a blood cell lineage, such as a white blood cell.

The term "circulating tumor DNA" or "ctDNA" refers to nucleic acid fragments that originate from tumor cells or other types of cancer cells, and which may be released into a bodily fluid of an individual (e.g., blood, sweat, urine, or saliva) as result of biological processes such as apoptosis or necrosis of dying cells or actively released by viable tumor cells.

The term "DNA fragment," "fragment," or "DNA molecule" may generally refer to any deoxyribonucleic acid fragments, i.e., cfDNA, gDNA, ctDNA, etc.

The term "anomalous fragment," "anomalously methylated fragment," or "fragment with an anomalous methylation pattern" refers to a fragment that has anomalous methylation of CpG sites. Anomalous methylation of a fragment may be determined using probabilistic models to identify unexpectedness of observing a fragment's methylation pattern in a control group.

The term "unusual fragment with extreme methylation" or "UFXM" refers to a hypomethylated fragment or a hypermethylated fragment. A hypomethylated fragment and a hypermethylated fragment refers to a fragment with at least some number of CpG sites (e.g., 5) that have over some threshold percentage (e.g., 90%) of methylation or unmethylation, respectively.

The term "anomaly score" refers to a score for a CpG site based on a number of anomalous fragments (or, in some embodiments, UFXMs) from a sample that overlaps that CpG site. The anomaly score is used in context of featurization of a sample for classification.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of 20%, +10%, +5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to +5%.

As used herein, the term "biological sample," "patient sample," or "sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map nucleic acid fragment sequences obtained from sequencing a sample from the subject. A reference genome can refer to a haploid or diploid genome to which nucleic acid fragment sequences from the biological sample and a constitutional sample can be aligned and compared. An example of a constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "cancer" or "tumor" refers to an abnormal mass of tissue in which the growth of the mass surpasses and is not coordinated with the growth of normal tissue.

As used herein, the phrase "healthy," refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites." In other instances, methylation may occur at a cytosine not part of a CpG site or at another nucleotide that's not cytosine; however, these are rarer occurrences. Anomalous cfDNA methylation can be identified as hypermethylation or hypomethylation, both of which may be indicative of cancer status. DNA methylation anomalies (compared to healthy controls) can cause different effects, which may contribute to cancer. The principles described herein are equally applicable for the detection of methylation in a CpG context and non-CpG context, including non-cytosine methylation. Further, the methylation state vectors may contain elements that are generally vectors of sites where methylation has or has not occurred (even if those sites are not CpG sites specifically).

As used interchangeably herein, the term "methylation fragment" or "nucleic acid methylation fragment" refers to a sequence of methylation states for each CpG site in a plurality of CpG sites, determined by a methylation sequencing of nucleic acids (e.g., a nucleic acid molecule and/or a nucleic acid fragment). In a methylation fragment, a location and methylation state for each CpG site in the nucleic acid fragment is determined based on the alignment of the sequence reads (e.g., obtained from sequencing of the nucleic acids) to a reference genome. A nucleic acid methylation fragment comprises a methylation state of each CpG site in a plurality of CpG sites (e.g., a methylation state vector), which specifies the location of the nucleic acid fragment in a reference genome (e.g., as specified by the position of the first CpG site in the nucleic acid fragment using a CpG index, or another similar metric) and the number of CpG sites in the nucleic acid fragment. As used herein, the term "CpG index" refers to a list of each CpG site in the plurality of CpG sites (e.g., CpG 1, CpG 2, CpG 3, etc.) in a reference genome, such as a human reference genome, which can be in electronic format. The CpG index further comprises a corresponding genomic location, in the corresponding reference genome, for each respective CpG site in the CpG index. Each CpG site in each respective nucleic acid methylation fragment is thus indexed to a specific location in the respective reference genome, which can be determined using the CpG index.

As used herein, the term "true positive" (TP) refers to a subject having a condition. "True positive" can refer to a subject that has a tumor, a cancer, a pre-cancerous condition (e.g., a pre-cancerous lesion), a localized or a metastasized cancer, or a non-malignant disease. "True positive" can refer to a subject having a condition and is identified as having the condition by an assay or method of the present disclosure. As used herein, the term "true negative" (TN) refers to a subject that does not have a condition or does not have a detectable condition. True negative can refer to a subject that does not have a disease or a detectable disease, such as a tumor, a cancer, a pre-cancerous condition (e.g., a pre-cancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 450 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing" and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the term "sequencing depth," is interchangeably used with the term "coverage" and refers to the number of times a locus is covered by a consensus sequence read corresponding to a unique nucleic acid target molecule aligned to the locus; e.g., the sequencing depth is equal to the number of unique nucleic acid target molecules covering the locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a locus or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. In some embodiments, a subject is a male or female of any stage (e.g., a man, a woman or a child). A subject from whom a sample is taken, or is treated by any of the methods or compositions described herein can be of any age and can be an adult, infant or child.

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein, the term "genomic" refers to a characteristic of the genome of an organism. Examples of genomic characteristics include, but are not limited to, those relating to the primary nucleic acid sequence of all or a portion of the genome (e.g., the presence or absence of a nucleotide polymorphism, indel, sequence rearrangement, mutational frequency, etc.), the copy number of one or more particular nucleotide sequences within the genome (e.g., copy number, allele frequency fractions, single chromosome or entire genome ploidy, etc.), the epigenetic status of all or a portion of the genome (e.g., covalent nucleic acid modifications such as methylation, histone modifications, nucleosome positioning, etc.), the expression profile of the organism's genome (e.g., gene expression levels, isotype expression levels, gene expression ratios, etc.).

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having,"

"has," "with," or variants thereof are used in either the detailed description and/or the claims, such terms are intended to be inclusive in a manner similar to the term "comprising."

II. Sample Processing

II.A. Contamination Detection

FIG. 1 is an exemplary flowchart describing a process 100 of contamination detection in a sample, according to one or more embodiments. Generally, samples may be from individuals that are healthy, that are known to have or suspected of having cancer, or where no prior information is known. The sample may be selected from the group consisting of blood, plasma, serum, urine, fecal, and saliva samples. Alternatively, the sample may be selected from the group consisting of whole blood, a blood fraction (e.g., white blood cells (WBCs)), a tissue biopsy, pleural fluid, pericardial fluid, cerebral spinal fluid, and peritoneal fluid. The analytics system may perform the contamination detection process 100 on any type of sample. For example, the analytics system may perform the process 100 on training samples prior to use in training various models. As another example, the analytics system may perform the process 100 on test samples prior to downstream analyses and provide those analyses back to the individual and their healthcare provider.

Prior to cancer classification with the sample, the process 100 of contamination detection ensures samples proceeding to cancer classification are not contaminated with foreign fragments from another individual or organism. In one or more embodiments, a sample with an above-threshold number of contamination fragments may be labeled as contaminated and withheld from further analyses. In other embodiments, each contamination fragment may be removed from the sample with the remaining fragments used in downstream analyses. The contamination detection utilizes a set of genetic sequences as contamination markers to identify fragments that have an allele different from the individual's homozygous allele. The process 100 is described herein as being performed by an analytics system (an example of which is provided in FIGS. 6A & 6B and corresponding description), but some or all of the steps may be performed by other comparably described sequencing devices and/or computer processors.

The analytics system sequences 110 the cfDNA fragments in the sample with a target panel including contamination marker probes. The contamination markers are genetic sequences in the human genome and may include CpG-SNP sites which include at least one SNP at one CpG site. Contamination marker probes may be designed to target the contamination marker sequence on a single strand of the DNA or both strands of the DNA. Probes may also be designed to target one, some, or all haplotypes of the contamination marker sequence, e.g., for a CpG-SNP site, the probes may target one, some, or all of the haplotypes. Designing probes that target all of the potential haplotypes of a contamination marker avoids reference bias to any one particular haplotype. Contamination marker selection and subsequent probe design is discussed below in FIG. 2. As a result of the sequencing, the analytics system has sequence reads of the cfDNA fragments in the sample.

The analytics system identifies 120 one or more CpG-SNP markers from the plurality for which the sample has a homozygous haplotype. To determine the haplotype of the sample at each CpG-SNP marker, the analytics system evaluates the haplotypes of all sequence reads for cfDNA fragments at that CpG-SNP marker location. If the analytics system observes a very high percentage, e.g., above 90%, 91%, 92%, 93%, 94%, 95%, 96%, 97%, 98%, or 99%, of sequence reads having one haplotype, then the analytics system determines the sample is homozygous for that haplotype (i.e., both copies of the contamination marker in the sample are of the same haplotype). CpG-SNP markers where sequence reads do not surpass the high percentage are determined not to be homozygous and may rather be determined to be heterozygous (i.e., the two copies of the contamination marker in the sample are of differing haplotype). For example, at a first contamination marker that comprises a single CpG-SNP site, there are two haplotypes: (1) presence of SNP removing the existing CpG, or (2) absence of SNP, thereby the existing CpG remains. The analytics system at the first contamination marker determines that 99% of the fragments overlapping that first contamination marker show the first haplotype, which is above the threshold percentage of 95% (for example). In some embodiments, the analytics system may use a minimum coverage at a contamination marker in order to use the contamination marker. For example, if a contamination marker has 10 fragments overlapping that marker, which is too few, then the analytics system excludes use of that contamination marker from the contamination detection process 100. This would prevent low-coverage contamination markers that may skew the process 100 due to lack of signal.

For each identified contamination marker, the analytics system 130 identifies cfDNA fragments having a different haplotype at the identified CpG-SNP marker than the homozygous haplotype of the sample as contamination cfDNA fragments. Of the plurality of CpG-SNP markers utilized, any given sample likely has a homozygous haplotype for a subset of one or more CpG-SNP markers of the initial plurality. The analytics system for the identified CpG-SNP markers for which the sample has a homozygous haplotype, can reasonably exclude fragments that have a different haplotype as contamination fragments. For example, the sample has a homozygous haplotype of no SNP at a CpG-SNP marker. The analytic system labels any fragment that has a different haplotype than the homozygous haplotype, e.g., a SNP at that CpG-SNP marker, as a contamination cfDNA fragment.

In a single CpG-SNP site contamination marker, the analytics system identifies the differential hits in a sequence read to determine whether the haplotype is different than the homozygous haplotype. For example, the single CpG-SNP site contamination marker involves a SNP changing a guanine to adenine in the CpG dinucleotide that is highly methylated. Presence of the SNP would reflect two differential hits in a bisulfite sequencing context. The cytosine would show as unmethylated rather than methylated, via conversion to uracil in the bisulfite process, and the guanine would show as an adenine. If the homozygous haplotype is absence of the SNP, then the analytics system can call the opposite haplotype if both differential hits were identified. If one differential hit was identified, then the analytics system may rather determine the sequence read be due to some sequencing error and not the opposite haplotype. A similar principle may apply to contamination markers of varied numbers of differential hits used. As another example, if a haplotype is determined by six differential hits, then at least five hits are used to affirmatively identify the haplotype. The analytics system determines or calls the fragments determined to have differing haplotypes from the homozygous haplotype as contamination fragments.

The analytics system may further assign a confidence score to the contamination call based on the differential hits identified. The confidence score inversely corresponds to a likelihood that the contamination call was due to some other error (sequencing error, amplification error, etc.) rather than contamination. As such, a higher confidence score corresponds to a lower likelihood that the contamination call was due to some other error. A lower confidence score corresponds to a higher likelihood that the contamination call was due to some other error. The confidence score may also provide a relative confidence of a contamination call against other contamination calls. For example, a contamination call with a confidence score of 1 has less confidence, corresponding to a higher chance the contamination call was due to other error instead of contamination of the fragment, than another contamination call with a confidence score of 2. If all differential hits are identified to determine a fragment to have the opposite haplotype, then the confidence score is at a maximum. If the minimum number of differential hits are identified to determine the different haplotype, then the confidence score to the contamination call may be a lower-than-maximum score. The confidence score may further be based on other factors, e.g., coverage at the contamination marker, percentage of fragments having the homozygous haplotype, etc.

In one or more embodiments, the analytics system determines 140 the sample as contaminated based on one or more contamination cfDNA fragments. The analytics system may utilize some threshold quantity of contamination cfDNA fragments for marking the sample as contaminated. Above the threshold quantity, the analytics system marks the sample as contaminated. In one embodiment, the threshold quantity is a threshold number of contamination fragments, e.g., 1, 2, 3, 4, 5, 6, 7, 8, 9, 10, 11, 12, 13, 14, or 15. In one embodiment, the threshold quantity is a threshold percentage of contamination fragments in the sample, e.g., 0.01%, 0.02%, 0.03%, 0.04%, 0.05%, 0.06%, 0.07%, 0.08%, 0.09%, 0.10%, 0.20%, 0.30%, 0.40%, 0.50%, 0.60%, 0.70%, 0.80%, 0.90%, or 1.00%. In response to determining that the sample is contaminated, the analytics system may withhold the sample from downstream analyses, e.g., cancer classification.

If the sample is determined to be contaminated, the analytics system may perform one or more further actions. The analytics system may exclude 150 the sample for further analyses, such as cancer classification. In embodiments with training samples, the sample may be excluded from use in training the cancer classification. In embodiments with a test sample, the test sample may be excluded from determining a cancer prediction. If the test sample is not determined to be contaminated, then the downstream cancer classification may proceed. The analytics system may provide 160 a notification to a healthcare provider of the contaminated sample and/or to obtain a new sample. The analytics system may remove 170 contamination fragments and proceed with downstream analyses. The analytics system may perform one or more of the above actions.

The contamination detection process 100 importantly prevents analyzing a contaminated sample and relying on that analysis. In the context of training samples, the cancer classification models may be skewed if non-cancer samples are contaminated with fragments from a cancer sample. In the context of a contaminated test sample, the cancer classification analyses may return inaccurate results that may be provided back to a healthcare provider or individual being screened. Those inaccurate results can include misdiagnosing someone with a likelihood of cancer. Moreover, processing cfDNA fragments of a sample against other potentially contaminated cfDNA fragments is a computationally expensive procedure. This process is difficult to perform with a human mind as selecting the CpG sites that are indicative of contamination of a test sample and comparing them with other CpG sites of other cfDNA fragments may entail a high-level of computation that cannot be performed in the human mind, especially when the number of samples or the number of CpG sites are large.

FIG. 2 is an exemplary flowchart describing a process 200 of identifying CpG-SNP sites for use as contamination markers in contamination detection, according to one or more embodiments. The process 200 is described herein as being performed by the analytics system, but some or all of the steps may be performed by other comparably described sequencing devices and/or computer processors.

The analytics system identifies 205 CpG sites that are prone to SNP mutation. The analytics system may search over all CpG sites (e.g., via bisulfite sequencing, whole genome sequencing, targeted sequencing, etc.) to identify CpG sites prone to SNP mutation. A CpG-SNP site is a nucleotide sequence that involves a SNP mutation affecting a CpG presence in the sequence. The error rate for CpG-SNP sites can be ultra low. The error rate can be the likelihood that an observed sequence occurred through some sequencing error rather than being the true sequence of the cfDNA fragment. In the context of a contamination marker, the error rate can be the likelihood that an observed sequence, that is different than a sample's expected sequence at the contamination marker, occurred through sequencing error. As such, the lower the error rate, the higher the confidence in determining the cfDNA fragment to be a contaminated fragment. For CpG-SNP sites sequenced with bisulfite sequencing, the error rate can be a product of a bisulfite conversion error rate and a SNP error rate. In one example estimation, the SNP error rate ranges from 0.1% to 0.01%, whereas the bisulfite conversion error rate is about 0.4%. As such, the overall error rate is 0.0004% to 0.00004% (1 in 2.5 m).

CpG-SNP sites may include additive CpG-SNP sites and subtractive CpG-SNP sites. An additive CpG-SNP site (also referred to as a CpG-gain SNP) includes a SNP mutation that creates a CpG site that may not be present absent the SNP mutation. For example, additive CpG-SNP sites (in a tribase context) may include: XTG into XCG; XAG into XCG; XGG into XCG; CTX into CGX; CAX into CGX; and CCX into CGX (wherein X refers to any potential nucleotide). A subtractive CpG-SNP site (also referred to as a CpG-loss SNP) includes a SNP mutation that removes a CpG site that may be present absent the SNP. For example, subtractive CpG-SNP sites (in a tribase context) may include: XCG into XTG; XCG into XAG; XCG into XGG; CGX into CTX; CGX into CAX; and CGX into CCX (wherein X refers to any potential nucleotide). Some CpG-SNP sites may simultaneously remove a CpG site and create another CpG site shifted one base over. The analytics system may further differentiate between CpG-SNP sites that are (1) fully methylated, (2) fully unmethylated, or (3) neither fully methylated nor fully unmethylated.

The analytics system may utilize a training cohort of samples to identify the CpG-SNP sites. The training cohort may represent a diverse population. In some embodiments, the training cohort are healthy samples (e.g., samples from individuals without any disease diagnosis), to ensure identifying CpG sites that are not confounded by cancer samples (or other samples diagnosed with another disease). In other embodiments, the samples comprise both healthy samples and cancer samples. In one embodiment, the analytics system identifies each and every CpG site that is observed to have a SNP in at least one sample. This can yield the broadest set of CpG-SNP sites. In another embodiment, the analytics system identifies CpG sites with an observed SNP in at least some threshold number of samples (e.g., 2, 3, 4, 5, 6, 7, 8, 9, 10) or in at least some threshold percentage of samples (e.g., 0.01%, 0.05%, 0.1%, 0.5%, 1%, 5%, etc.). This can likely yield a smaller listing of CpG-SNP sites.

In some embodiments, the analytics system screens 210 for additional criteria for the contamination marker selection.

One criterion may ensure the CpG-SNP sites do not overlap one another. For example, consider a tribase sequence of CGG that includes a CpG site in the first two bases. One additive CpG-SNP site mutates the middle base of the CGG sequence into CCG creating a CpG in the latter two bases of the sequence. A different subtractive CpG-SNP site mutates the same CGG sequence into CAG thereby removing the CpG site present in the first two bases of the sequence. The analytics system may seek to remove such CpG-SNP sites.

Another criterion may seek to identify hybrid sites. One example hybrid site is a multiple CpG-SNP site. A multiple CpG-SNP site includes two or more CpG-SNP sites within the threshold distance. For example, a multiple CpG-SNP site comprises two additive CpG-SNP's within 20 basepairs. The threshold distance may be set at 10 bp, 15 bp, 20 bp, 25 bp, 30 bp, 35 bp, 40 bp, 45 bp, 50 bp. A multiple CpG-SNP site that encompasses two CpG-SNP's has an even stronger predictive power for contamination. The likelihood of error (sequencing or otherwise) affecting two CpG-SNP's can be rare (e.g., range of 1 in 50 million to 1 in 500 million).

Another example hybrid site is a CpG-SNP & indel site. The CpG-SNP & indel site comprises at least one CpG-SNP site and an indel within a threshold distance. As above, the threshold distance may be set at 10 bp, 15 bp, 20 bp, 25 bp, 30 bp, 35 bp, 40 bp, 45 bp, 50 bp. The indel may be either an insertion or a deletion of a particular sequence. The indel may be within a threshold length, e.g., the threshold length is set at 2 bp, 3, bp, 4 bp, 5 bp, 6 bp, 7 bp, 8 bp, 9 bp, or 10 bp. For example, the maximum threshold length set at 5 bp will filter out any indel sequences of length greater than 5 bp. There may be additional criteria for indel selection, e.g., removal of low complexity indels like homopolymers and simple tandem repeats. Homopolymers are strings of one repeated nucleotide, e.g., ACGTTTTTTTTTTTTTTTTACG (SEQ ID NO: 1) includes a homopolymer of fifteen thymines. For homopolymers, there may be a threshold repetition number to be considered low complexity, e.g., 5 or more repetitions would be considered low complexity. Simple tandem repeats are strings of repeated nucleotide tandems, e.g., ACGTCATCATCATCATCATCATCATACGT (SEQ ID NO: 2) includes seven repeated instances of the nucleotide tandem CAT. For simple tandem repeats, there may be a threshold number of repeats to be considered low complexity, e.g., 3 or more repetitions to be considered low complexity. High complexity sequences may include sequences of higher length without homopolymers or simple tandem repeats. High complexity indel sequences ensure screening against contaminated fragments as opposed to errors introduced via sample processing, e.g., polymerase chain reaction (PCR) or sequencing. In one or more embodiments, an indel site affecting at least one CpG-SNP site may be used as a contamination marker.

The hybrid sites can have lower error rates compared to the single CpG-SNP sites, such that the hybrid sites have a greater confidence in contamination detection. For example, the multiple CpG-SNP site may have an error rate in the range of 1 in 50 million to 1 in 500 million.

The analytics system includes 215 CpG-SNP sites with haplotypes having population haplotype frequencies within a threshold range. The threshold range may be ±1%, ±2%, ±3%, ±4%, ±5%, ±6%, ±7%, ±8%, ±9%, or ±10% of 50%. For example, a single CpG-SNP site may comprise a first haplotype with the SNP present and a second haplotype with the SNP absent. In one or more embodiments, the analytics system may exclude hybrid sites with more than two, three, or four haplotypes. The analytics system can retain the CpG-SNP site if the two haplotypes have population haplotype frequencies within the threshold range. In embodiments with more than two haplotypes, the analytics system may utilize CpG-SNP sites with two haplotypes having population haplotype frequencies within the threshold range with the remaining haplotypes having a negligible population haplotype frequency (e.g., less than 1%, 2%, 3%, 4%, 5%, 6%, 7%, 8%, 9%, or 10%). The population haplotype frequencies may be estimated using a training cohort of samples. In some embodiments, additional criteria define the training cohort, e.g., ethnic diversity representation, age diversity representation, biological sex diversity, excluding samples diagnosed with cancer or other diseases, or some combination thereof. The analytic system can sequence each sample in the training cohort and labels the haplotype of each CpG-SNP site based on the sequencing. The analytics system can calculate the population haplotype frequency for a CpG-SNP site based on the counts of each haplotype The analytics system ensures 220 haplotypes at each CpG-SNP site are in Hardy-Weinberg equilibrium. The analytics system calculates an allele frequency for each allele of the CpG-SNP site. The allele frequency can be calculated using data obtained from a genetic database or with a set of samples representing the population. The analytics system then checks whether the allele frequencies for each CpG-SNP site are in Hardy-Weinberg equilibrium:

$$p^2+2pq+q^2=1$$

where p is the allele frequency for a first allele of the CpG-SNP site and q is the allele frequency for a second allele of the CpG-SNP site. Checking whether each CpG-SNP site is in Hardy-Weinberg equilibrium ensures against artifacts arising out of CpG-SNP sites that may be evolving or mutating, i.e., such that they are not in equilibrium. The analytics system may incorporate some tolerance in the Hardy-Weinberg equilibrium calculation.

The analytics system may omit one or more of the steps 205, 210, 215, 220, and 225. In other embodiments, step 210 and/or step 220 may be omitted.

At this juncture, the analytics system has identified a plurality of CpG-SNP sites after one, some, or all of steps 205, 210, 215, and 220 as viable for use as contamination markers. The analytics system may further trim down the number of viable CpG-SNP sites based on a budget of contamination markers that may be implemented in the sequencing panel. The analytics system may optimize distribution of the CpG-SNP site contamination markers throughout the genome. The analytics system may also adjust the various parameters at the steps 205, 210, 215, and 220 to optimize how many CpG-SNP sites are selected as contamination markers. For example, the analytics system may exclude certain types of CpG-SNP sites to decrease the number of CpG-SNP sites that may be considered in step 210. As another example, the analytics system may decrease the threshold distance in step 210 in identifying hybrid sites. Appendix includes various tables of contamination markers. Table 1 includes a list of CpG-SNP sites selected for use as contamination markers, according to an example implementation. Table 2 includes a list of single CpG-SNP sites used as contamination markers. Table 3 includes a list of multiple CpG-SNP sites used as contamination markers. Table 4 includes a list of CpG-SNP & indel sites used as contamination markers. Table 4 discloses SEQ ID NO: 16.

The analytics system designs 225 contamination marker probes targeting each haplotype of the CpG-SNP site contamination markers. Depending on which two haplotypes are considered at step 215 for each CpG-SNP site contamination marker, the analytics system designs probes targeting each of the two haplotypes. The analytics system may also design probes targeting both DNA strands of each haplotype. Designing probes targeting each haplotype of the contamination marker avoids reference or alternative bias in sequencing. In another embodiment, the analytics system designs a single probe targeting the reference sequence of each CpG-SNP site contamination marker.

Therefore, as described above, the method using contamination markers to identify potentially contaminated cfDNA fragments with differing haplotypes for one or more CpG sites allows more accurate data to be collected, for example, for purposes of training and performing inference using the cancer detection model.

II.B. Generating Methylation State Vectors for DNA Fragments

FIG. 3A is an exemplary flowchart describing a process 300 of sequencing a fragment of cfDNA to obtain a methylation state vector, according to one or more embodiments. In order to analyze DNA methylation, an analytics system first obtains 310 a sample from an individual comprising a plurality of cfDNA molecules. In additional embodiments, the process 300 may be applied to sequence other types of DNA molecules.

From the sample, the analytics system can isolate each cfDNA molecule. The cfDNA molecules can be treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA molecules, a sequencing library can be prepared 330. During library preparation, unique molecular identifiers (UMI) can be added to the nucleic acid molecules (e.g., DNA molecules) through adapter ligation. The UMIs can be short nucleic acid sequences (e.g., 4-10 base pairs) that are added to ends of DNA fragments (e.g., DNA molecules fragmented by physical shearing, enzymatic digestion, and/or chemical fragmentation) during adapter ligation. UMIs can be degenerate base pairs that serve as a unique tag that can be used to identify sequence reads originating from a specific DNA fragment.

During PCR amplification following adapter ligation, the UMIs can be replicated along with the attached DNA fragment. This can provide a way to identify sequence reads that came from the same original fragment in downstream analysis.

Optionally, the sequencing library may be enriched 135 for cfDNA molecules, or genomic regions, that are informative for cancer status using a plurality of hybridization probes. The hybridization probes are short oligonucleotides capable of hybridizing to particularly specified cfDNA molecules, or targeted regions, and enriching for those fragments or regions for subsequent sequencing and analysis. Hybridization probes may be used to perform a targeted, high-depth analysis of a set of specified CpG sites of interest to the researcher. Hybridization probes can be tiled across one or more target sequences at a coverage of 1×, 2×, 3×, 4×, 5×, 6×, 7×, 8×, 9×, 10×, or more than 10×. For example, hybridization probes tiled at a coverage of 2× comprises overlapping probes such that each portion of the target sequence is hybridized to 2 independent probes. Hybridization probes can be tiled across one or more target sequences at a coverage of less than 1×.

In one embodiment, the hybridization probes are designed to enrich for DNA molecules that have been treated (e.g., using bisulfite) for conversion of unmethylated cytosines to uracils. During enrichment, hybridization probes (also referred to herein as "probes") can be used to target and pull down nucleic acid fragments informative for the presence or absence of cancer (or disease), cancer status, or a cancer classification (e.g., cancer class or tissue of origin). The probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. The probes can be designed based on a methylation site panel. The probes can be designed based on a panel of targeted genes to analyze particular mutations or target regions of the genome (e.g., of the human or another organism) that are suspected to correspond to certain cancers or other types of diseases. Moreover, the probes may cover overlapping portions of a target region.

Once prepared, the sequencing library or a portion thereof can be sequenced to obtain a plurality of sequence reads. The sequence reads may be in a computer-readable, digital format for processing and interpretation by computer software. The sequence reads may be aligned to a reference genome to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. A sequence read can be comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome can represent the likely location within the reference genome to which the nucleic acid fragment corresponds. An output file having SAM (sequence alignment map) format or BAM (binary) format may be generated and output for further analysis such as methylation state determination.

From the sequence reads, the analytics system determines 350 a location and methylation state for each CpG site based on alignment to a reference genome. The analytics system generates 360 a methylation state vector for each fragment specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). Observed states can be states of methylated and unmethylated; whereas, an unobserved state is indeterminate. Indeterminate methylation states may originate from sequencing errors and/or disagreements between methylation states of a DNA fragment's complementary strands. The methylation state vectors may be stored in temporary or persistent computer memory for later use and processing. Further, the analytics system may remove duplicate reads or duplicate methylation state vectors from a single sample. The analytics system may determine that a certain fragment with one or more CpG sites has an indeterminate methylation status over a threshold number or percentage, and may exclude such fragments or selectively include such fragments but build a model accounting for such indeterminate methylation statuses; one such model will be described below in conjunction with FIG. 4.

FIG. 3B is an exemplary illustration of the process 300 of FIG. 3A of sequencing a cfDNA molecule to obtain a methylation state vector, according to one or more embodiments. As an example, the analytics system receives a cfDNA molecule 312 that, in this example, contains three CpG sites. As shown, the first and third CpG sites of the cfDNA molecule 312 are methylated 314. During the treatment step 320, the cfDNA molecule 312 is converted to generate a converted cfDNA molecule 322. During the treatment 320, the second CpG site which was unmethylated has its cytosine converted to uracil. However, the first and third CpG sites were not converted.

After conversion, a sequencing library 330 is prepared and sequenced 340 to generate a sequence read 342. The analytics system aligns 350 the sequence read 342 to a reference genome 344. The reference genome 344 provides the context as to what position in a human genome the fragment cfDNA originates from. In this simplified example, the analytics system aligns 350 the sequence read 342 such that the three CpG sites correlate to CpG sites 23, 24, and 25 (arbitrary reference identifiers used for convenience of description). The analytics system can thus generate information both on methylation status of all CpG sites on the cfDNA molecule 312 and the position in the human genome that the CpG sites map to. As shown, the CpG sites on sequence read 342 which are methylated are read as cytosines. In this example, the cytosines appear in the sequence read 342 only in the first and third CpG site which allows one to infer that the first and third CpG sites in the original cfDNA molecule are methylated. Whereas, the second CpG site can be read as a thymine (U is converted to T during the sequencing process), and thus, one can infer that the second CpG site is unmethylated in the original cfDNA molecule. With these two pieces of information, the methylation status and location, the analytics system generates 360 a methylation state vector 352 for the fragment cfDNA 312. In this example, the resulting methylation state vector 352 is <$M_{23}$, $U_{24}$, $M_{25}$>, wherein M corresponds to a methylated CpG site, U corresponds to an unmethylated CpG site, and the subscript number corresponds to a position of each CpG site in the reference genome.

One or more alternative sequencing methods can be used for obtaining sequence reads from nucleic acids in a biological sample. The one or more sequencing methods can comprise any form of sequencing that can be used to obtain a number of sequence reads measured from nucleic acids (e.g., cell-free nucleic acids), including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single-molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and Nanopore sequencing can also be used to obtain sequence reads from the nucleic acids (e.g., cell-free nucleic acids) in the biological sample. Sequencing-by-synthesis and reversible terminator-based sequencing (e.g., Illumina's Genome Analyzer; Genome Analyzer II; HISEQ 2000; HISEQ 4500 (Illumina, San Diego Calif.)) can be used to obtain sequence reads from the cell-free nucleic acid obtained from a biological sample of a training subject in order to form the genotypic dataset. Millions of cell-free nucleic acid (e.g., DNA) fragments can be sequenced in parallel. In one example of this type of sequencing technology, a flow cell is used that contains an optically transparent slide with eight individual lanes on the surfaces of which are bound oligonucleotide anchors (e.g., adaptor primers). A cell-free nucleic acid sample can include a signal or tag that facilitates detection. The acquisition of sequence reads from the cell-free nucleic acid obtained from the biological sample can include obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

The one or more sequencing methods can comprise a whole-genome sequencing assay. A whole-genome sequencing assay can comprise a physical assay that generates sequence reads for a whole genome or a substantial portion of the whole genome which can be used to determine large variations such as copy number variations or copy number aberrations. Such a physical assay may employ whole-genome sequencing techniques or whole-exome sequencing techniques. A whole-genome sequencing assay can have an average sequencing depth of at least 1×, 2×, 3×, 4×, 5×, 6×, 7×, 8×, 9×, 10×, at least 20×, at least 30×, or at least 40× across the genome of the test subject. In some embodiments, the sequencing depth is about 30,000×. The one or more sequencing methods can comprise a targeted panel sequencing assay. A targeted panel sequencing assay can have an average sequencing depth of at least 50,000×, at least 55,000×, at least 60,000×, or at least 70,000× sequencing depth for the targeted panel of genes. The targeted panel of genes can comprise between 450 and 500 genes. The targeted panel of genes can comprise a range of 500±5 genes, a range of 500±10 genes, or a range of 500±25 genes.

The one or more sequencing methods can comprise paired-end sequencing. The one or more sequencing methods can generate a plurality of sequence reads. The plurality of sequence reads can have an average length ranging between 10 and 700, between 50 and 400, or between 100 and 300. The one or more sequencing methods can comprise a methylation sequencing assay. The methylation sequencing can be i) whole-genome methylation sequencing or ii) targeted DNA methylation sequencing using a plurality of nucleic acid probes. For example, the methylation sequencing is whole-genome bisulfite sequencing (e.g., WGBS). The methylation sequencing can be a targeted DNA methylation sequencing using a plurality of nucleic acid probes targeting the most informative regions of the methylome, a unique methylation database and prior prototype whole-genome and targeted sequencing assays.

The methylation sequencing can detect one or more 5-methylcytosine (5mC) and/or 5-hydroxymethylcytosine (5hmC) in respective nucleic acid methylation fragments. The methylation sequencing can comprise conversion of one or more unmethylated cytosines or one or more methylated cytosines, in respective nucleic acid methylation fragments, to a corresponding one or more uracils. The one or more uracils can be detected during the methylation sequencing as one or more corresponding thymines. The conversion of one or more unmethylated cytosines or one or more methylated cytosines can comprise a chemical conversion, an enzymatic conversion, or combinations thereof.

For example, bisulfite conversion involves converting cytosine to uracil while leaving methylated cytosines (e.g., 5-methylcytosine or 5-mC) intact. In some DNA, about 95% of cytosines may not be methylated in the DNA, and the resulting DNA fragments may include many uracils which are represented by thymines. Enzymatic conversion processes may be used to treat the nucleic acids prior to sequencing, which can be performed in various ways. One example of a bisulfite-free conversion comprises a bisulfite-free and base-resolution sequencing method, TET-assisted pyridine borane sequencing (TAPS), for non-destructive and direct detection of 5-methylcytosine and 5-hydroxymethyl-cytosine without affecting unmodified cytosines. The methylation state of a CpG site in the corresponding plurality of CpG sites in the respective nucleic acid methylation fragment can be methylated when the CpG site is determined by the methylation sequencing to be methylated, and unmethylated when the CpG site is determined by the methylation sequencing to not be methylated.

A methylation sequencing assay (e.g., WGBS and/or targeted methylation sequencing) can have an average sequencing depth including but not limited to up to about 1,000×, 2,000×, 3,000×, 5,000×, 10,000×, 15,000×, 20,000×, or 30,000×. The methylation sequencing can have a sequencing depth that is greater than 30,000×, e.g., at least 40,000× or 50,000×. A whole-genome bisulfite sequencing method can have an average sequencing depth of between 20× and 50×, and a targeted methylation sequencing method has an average effective depth of between 100× and 1000×, where effective depth can be the equivalent whole-genome bisulfite sequencing coverage for obtaining the same number of sequence reads obtained by targeted methylation sequencing.

For further details regarding methylation sequencing (e.g., WGBS and/or targeted methylation sequencing), see, e.g., U.S. patent application Ser. No. 16/352,602, entitled "Methylation Fragment Anomaly Detection," filed Mar. 13, 2019, and U.S. patent application Ser. No. 16/719,902, entitled "Systems and Methods for Estimating Cell Source Fractions Using Methylation Information," filed Dec. 18, 2019, each of which is hereby incorporated by reference. Other methods for methylation sequencing, including those disclosed herein and/or any modifications, substitutions, or combinations thereof, can be used to obtain fragment methylation patterns. A methylation sequencing can be used to identify one or more methylation state vectors, as described, for example, in U.S. patent application Ser. No. 16/352,602, entitled "Anomalous Fragment Detection and Classification," filed Mar. 13, 2019, or in accordance with any of the techniques disclosed in U.S. patent application Ser. No. 15/931,022, entitled "Model-Based Featurization and Classification," filed May 13, 2020, each of which is hereby incorporated by reference.

The methylation sequencing of nucleic acids and the resulting one or more methylation state vectors can be used to obtain a plurality of nucleic acid methylation fragments. Each corresponding plurality of nucleic acid methylation fragments (e.g., for each respective genotypic dataset) can comprise more than 100 nucleic acid methylation fragments. An average number of nucleic acid methylation fragments across each corresponding plurality of nucleic acid methylation fragments can comprise 1000 or more nucleic acid methylation fragments, 5000 or more nucleic acid methylation fragments, 10,000 or more nucleic acid methylation fragments, 20,000 or more nucleic acid methylation fragments, or 30,000 or more nucleic acid methylation fragments. An average number of nucleic acid methylation fragments across each corresponding plurality of nucleic acid methylation fragments can be between 10,000 nucleic acid methylation fragments and 50,000 nucleic acid methylation fragments. The corresponding plurality of nucleic acid methylation fragments can comprise one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments. An average length of a corresponding plurality of nucleic acid methylation fragments can be between 140 and 480 nucleotides.

Further details regarding methods for sequencing nucleic acids and methylation sequencing data are disclosed in U.S. Provisional patent application Ser. No. 17/191,914, titled "Systems and Methods for Cancer Condition Determination Using Autoencoders," filed Mar. 4, 2021, which is hereby incorporated herein by reference in its entirety.

II.C. Identifying Anomalous Fragments

The analytics system can determine anomalous fragments for a sample using the sample's methylation state vectors. For each fragment in a sample, the analytics system can determine whether the fragment is an anomalous fragment using the methylation state vector corresponding to the fragment. In some embodiments, the analytics system calculates a p-value score for each methylation state vector describing a probability of observing that methylation state vector or other methylation state vectors even less probable in the healthy control group. The process for calculating a p-value score is further discussed below in Section II.C.i. P-Value Filtering. The analytics system may determine fragments with a methylation state vector having below a threshold p-value score as anomalous fragments. In some embodiments, the analytics system further labels fragments with at least some number of CpG sites that have over some threshold percentage of methylation or unmethylation as hypermethylated and hypomethylated fragments, respectively. A hypermethylated fragment or a hypomethylated fragment may also be referred to as an unusual fragment with extreme methylation (UFXM). In other embodiments, the analytics system may implement various other probabilistic models for determining anomalous fragments. Examples of other probabilistic models include a mixture model, a deep probabilistic model, etc. In some embodiments, the analytics system may use any combination of the processes described below for identifying anomalous fragments. With the identified anomalous fragments, the analytics system may filter the set of methylation state vectors for a sample for use in other processes, e.g., for use in training and deploying a cancer classifier.

II.C.I. P-Value Filtering

Figure 4A:
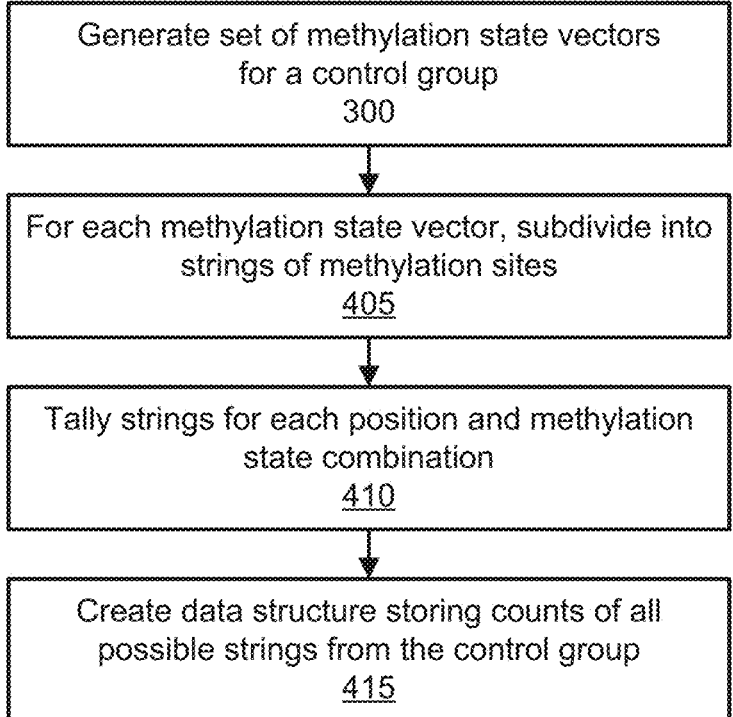

In some embodiments, the analytics system calculates a p-value score for each methylation state vector compared to methylation state vectors from fragments in a healthy control group. The p-value score can describe a probability of observing the methylation status matching that methylation state vector or other methylation state vectors even less probable in the healthy control group. In order to determine a DNA fragment to be anomalously methylated, the analytics system can use a healthy control group with a majority of fragments that are normally methylated. When conducting this probabilistic analysis for determining anomalous fragments, the determination can hold weight in comparison with the group of control subjects that make up the healthy control group. To ensure robustness in the healthy control group, the analytics system may select some threshold number of healthy individuals to source samples including DNA fragments. FIG. 4A below describes the method of generating a data structure for a healthy control group with which the analytics system may calculate p-value scores. FIG. 4B describes the method of calculating a p-value score with the generated data structure.

FIG. 4A is a flowchart describing a process 400 of generating a data structure for a healthy control group, according to an embodiment. To create a healthy control group data structure, the analytics system can receive a plurality of DNA fragments (e.g., cfDNA) from a plurality of healthy individuals. A methylation state vector can be identified for each fragment, for example via the process 300.

With each fragment's methylation state vector, the analytics system can subdivide 205 the methylation state vector into strings of CpG sites. In some embodiments, the analytics system subdivides 205 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 can result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 410 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are 2^3 or 8 possible string configurations. At that given CpG site, for each of the 8 possible string configurations, the analytics system tallies 410 how many occurrences of each methylation state vector possibility come up in the control group. Continuing this example, this may involve tallying the following quantities: $<M_x, M_{x+1}, M_{x+2}>, <M_x, M_{x+1}, U_{x+2}>, \ldots, <U_x, U_{x+1}, U_{x+2}>$ for each starting CpG site x in the reference genome. The analytics system creates 415 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least 2^4 numbers to tally for strings of length 4. Increasing the maximum string length to 5 means that every CpG site has an additional 2^4 or 16 numbers to tally, doubling the numbers to tally (and computer memory required) compared to the prior string length. Reducing string size can help keep the data structure creation and performance (e.g., use for later accessing as described below), in terms of computational and storage, reasonable. Second, a statistical consideration to limiting the maximum string length can be to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it uses a significant amount of data that may not be available, and thus can be too sparse for a model to perform appropriately. For example, calculating a probability of anomalousness/cancer conditioned on the prior 100 CpG sites can use counts of strings in the data structure of length 100, ideally some matching exactly the prior 100 methylation states. If only sparse counts of strings of length 100 are available, there can be insufficient data to determine whether a given string of length of 100 in a test sample is anomalous or not.

FIG. 4B is a flowchart describing a process 420 for identifying anomalously methylated fragments from an individual, according to an embodiment. In process 420, the analytics system generates 100 methylation state vectors from cfDNA fragments of the subject. The analytics system can handle each methylation state vector as follows.

For a given methylation state vector, the analytics system enumerates 430 all possibilities of methylation state vectors having the same starting CpG site and same length (i.e., set of CpG sites) in the methylation state vector. As each methylation state is generally either methylated or unmethylated there can be effectively two possible states at each CpG site, and thus the count of distinct possibilities of methylation state vectors can depend on a power of 2, such that a methylation state vector of length n would be associated with $2^n$ possibilities of methylation state vectors. With methylation state vectors inclusive of indeterminate states for one or more CpG sites, the analytics system may enumerate 430 possibilities of methylation state vectors considering only CpG sites that have observed states.

The analytics system calculates 440 the probability of observing each possibility of methylation state vector for the identified starting CpG site and methylation state vector length by accessing the healthy control group data structure. In some embodiments, calculating the probability of observing a given possibility uses a Markov chain probability to model the joint probability calculation. The Markov model can be trained, at least in part, based upon evaluation of a methylation state of each CpG site in the corresponding plurality of CpG sites of the respective fragment (e.g., nucleic acid methylation fragment) across those nucleic acid methylation fragments in a healthy noncancer cohort dataset that have the corresponding plurality of CpG sites. For example, a Markov model (e.g., a Hidden Markov Model or HMM) is used to determine the probability that a sequence of methylation states (comprising, e.g., "M" or "U") can be observed for a nucleic acid methylation fragment in a plurality of nucleic acid methylation fragments, given a set of probabilities that determine, for each state in the sequence, the likelihood of observing the next state in the sequence. The set of probabilities can be obtained by training the HMM. Such training can involve computing statistical parameters (e.g., the probability that a first state can transition to a second state (the transition probability) and/or the probability that a given methylation state can be observed for a respective CpG site (the emission probability)), given an initial training dataset of observed methylation state sequences (e.g., methylation patterns). HMMs can be trained using supervised training (e.g., using samples where the underlying sequence as well as the observed states are known) and/or unsupervised training (e.g., Viterbi learning, maximum likelihood estimation, expectation-maximization training, and/or Baum-Welch training). In other embodiments, calculation methods other than Markov chain probabilities are used to determine the probability of observing each possible methylation state vector. For example, the calculation method can include a learned representation. The p-value threshold can be between 0.01 and 0.10, or between 0.03 and 0.06. The p-value threshold can be 0.05. The p-value threshold can be less than 0.01, less than 0.001, or less than 0.0001.

The analytics system calculates 450 a p-value score for the methylation state vector using the calculated probabilities for each possibility. In some embodiments, this includes identifying the calculated probability corresponding to the possibility that matches the methylation state vector in question. Specifically, this can be the possibility having the same set of CpG sites, or similarly the same starting CpG site and length as the methylation state vector. The analytics system can sum the calculated probabilities of any possibilities having probabilities less than or equal to the identified probability to generate the p-value score.

This p-value can represent the probability of observing the methylation state vector of the fragment or other methylation state vectors even less probable in the healthy control group. A low p-value score can, thereby, generally correspond to a methylation state vector which is rare in a healthy individual, and which causes the fragment to be labeled anomalously methylated, relative to the healthy control group. A high p-value score can generally relate to a methylation state vector that is expected to be present, in a relative sense, in a healthy individual. If the healthy control group is a non-cancerous group, for example, a low p-value can indicate that the fragment is anomalously methylated relative to the non-cancer group, and therefore possibly indicative of the presence of cancer in the test subject.

As above, the analytics system can calculate p-value scores for each of a plurality of methylation state vectors, each representing a cfDNA fragment in the test sample. To identify which of the fragments are anomalously methylated, the analytics system may filter 460 the set of methylation state vectors based on their p-value scores. In some embodiments, filtering is performed by comparing the p-values scores against a threshold and keeping only those fragments below the threshold. This threshold p-value score can be on the order of 0.1, 0.01, 0.001, 0.0001, or similar.

According to example results from the process 400, the analytics system can yield a median (range) of 2,800 (1,500-12,000) fragments with anomalous methylation patterns for participants without cancer in training, and a median (range) of 3,000 (1,200-420,000) fragments with anomalous methylation patterns for participants with cancer in training. These filtered sets of fragments with anomalous methylation patterns may be used for the downstream analyses as described below in Section III.

In some embodiments, the analytics system uses 455 a sliding window to determine possibilities of methylation state vectors and calculate p-values. Rather than enumerating possibilities and calculating p-values for entire methylation state vectors, the analytics system can enumerate possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window can identify the sequential set of CpG sites from the vector within the window starting from the first CpG site in the vector. The analytic system can calculate a p-value score for the window including the first CpG site. The analytics system can then "slide" the window to the second CpG site in the vector, and calculate another p-value score for the second window. Thus, for a window size l and methylation vector length m, each methylation state vector can generate m−l+1 p-value scores. After completing the p-value calculations for each portion of the vector, the lowest p-value score from all sliding windows can be taken as the overall p-value score for the methylation state vector. In other embodiments, the analytics system aggregates the p-value scores for the methylation state vectors to generate an overall p-value score.

Using the sliding window can help to reduce the number of enumerated possibilities of methylation state vectors and their corresponding probability calculations that would otherwise need to be performed. To give a realistic example, it can be for fragments to have upwards of 54 CpG sites. Instead of computing probabilities for $2^{54}$ (~$1.8 \times 10^{16}$) possibilities to generate a single p-score, the analytics system can instead use a window of size 5 (for example) which results in 50 p-value calculations for each of the 50 windows of the methylation state vector for that fragment. Each of the 50 calculations can enumerate $2^{5}$ (32) possibilities of methylation state vectors, which total results in $50 \times 2^{5}$ ($1.6 \times 10^{3}$) probability calculations. This can result in a vast reduction of calculations to be performed, with no meaningful hit to the accurate identification of anomalous fragments.

In embodiments with indeterminate states, the analytics system may calculate a p-value score summing out CpG sites with indeterminates states in a fragment's methylation state vector. The analytics system can identify all possibilities that have consensus with the all methylation states of the methylation state vector excluding the indeterminate states.

The analytics system may assign the probability to the methylation state vector as a sum of the probabilities of the identified possibilities. As an example, the analytics system can calculate a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states can use calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In some embodiments, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities can allow for efficient calculation of p-score values without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

One or more nucleic acid methylation fragments can be filtered prior to training region models or cancer classifiers. Filtering nucleic acid methylation fragments can comprise removing, from the corresponding plurality of nucleic acid methylation fragments, each respective nucleic acid methylation fragment that fails to satisfy one or more selection criteria (e.g., below or above one selection criteria). The one or more selection criteria can comprise a p-value threshold. The output p-value of the respective nucleic acid methylation fragment can be determined, at least in part, based upon a comparison of the corresponding methylation pattern of the respective nucleic acid methylation fragment to a corresponding distribution of methylation patterns of those nucleic acid methylation fragments in a healthy noncancer cohort dataset that have the corresponding plurality of CpG sites of the respective nucleic acid methylation fragment.

Filtering a plurality of nucleic acid methylation fragments can comprise removing each respective nucleic acid methylation fragment that fails to satisfy a p-value threshold. The filter can be applied to the methylation pattern of each respective nucleic acid methylation fragment using the methylation patterns observed across the first plurality of nucleic acid methylation fragments. Each respective methylation pattern of each respective nucleic acid methylation fragment (e.g., Fragment One, . . . , Fragment N) can comprise a corresponding one or more methylation sites (e.g., CpG sites) identified with a methylation site identifier and a corresponding methylation pattern, represented as a sequence of 1's and 0's, where each "1" represents a methylated CpG site in the one or more CpG sites and each "0" represents an unmethylated CpG site in the one or more CpG sites. The methylation patterns observed across the first plurality of nucleic acid methylation fragments can be used to build a methylation state distribution for the CpG site states collectively represented by the first plurality of nucleic acid methylation fragments (e.g., CpG site A, CpG site B, . . ., CpG site ZZZ). Further details regarding processing of nucleic acid methylation fragments are disclosed in U.S. Provisional patent application Ser. No. 17/191,914, titled "Systems and Methods for Cancer Condition Determination Using Autoencoders," filed Mar. 4, 2021, which is hereby incorporated herein by reference in its entirety.

The respective nucleic acid methylation fragment may fail to satisfy a selection criterion in the one or more selection criteria when the respective nucleic acid methylation fragment has an anomalous methylation score that is less than an anomalous methylation score threshold. In this situation, the anomalous methylation score can be determined by a mixture model. For example, a mixture model can detect an anomalous methylation pattern in a nucleic acid methylation fragment by determining the likelihood of a methylation state vector (e.g., a methylation pattern) for the respective nucleic acid methylation fragment based on the number of possible methylation state vectors of the same length and at the same corresponding genomic location. This can be executed by generating a plurality of possible methylation states for vectors of a specified length at each genomic location in a reference genome. Using the plurality of possible methylation states, the number of total possible methylation states and subsequently the probability of each predicted methylation state at the genomic location can be determined. The likelihood of a sample nucleic acid methylation fragment corresponding to a genomic location within the reference genome can then be determined by matching the sample nucleic acid methylation fragment to a predicted (e.g., possible) methylation state and retrieving the calculated probability of the predicted methylation state. An anomalous methylation score can then be calculated based on the probability of the sample nucleic acid methylation fragment.

The respective nucleic acid methylation fragment can fail to satisfy a selection criterion in the one or more selection criteria when the respective nucleic acid methylation fragment has less than a threshold number of residues. The threshold number of residues can be between 10 and 50, between 50 and 100, between 100 and 150, or more than 150. The threshold number of residues can be a fixed value between 20 and 90. The respective nucleic acid methylation fragment may fail to satisfy a selection criterion in the one or more selection criteria when the respective nucleic acid methylation fragment has less than a threshold number of CpG sites. The threshold number of CpG sites can be 4, 5, 6, 7, 8, 9, or 10. The respective nucleic acid methylation fragment can fail to satisfy a selection criterion in the one or more selection criteria when a genomic start position and a genomic end position of the respective nucleic acid methylation fragment indicates that the respective nucleic acid methylation fragment represents less than a threshold number of nucleotides in a human genome reference sequence.

The filtering can remove a nucleic acid methylation fragment in the corresponding plurality of nucleic acid methylation fragments that has the same corresponding methylation pattern and the same corresponding genomic start position and genomic end position as another nucleic acid methylation fragment in the corresponding plurality of nucleic acid methylation fragments. This filtering step can remove redundant fragments that are exact duplicates, including, in some instances, PCR duplicates. The filtering can remove a nucleic acid methylation fragment that has the same corresponding genomic start position and genomic end position and less than a threshold number of different methylation states as another nucleic acid methylation fragment in the corresponding plurality of nucleic acid methylation fragments. The threshold number of different methylation states used for retention of a nucleic acid methylation fragment can be 1, 2, 3, 4, 5, or more than 5. For example, a first nucleic acid methylation fragment having the same corresponding genomic start and end position as a second nucleic acid methylation fragment but having at least 1, at least 2, at least 3, at least 4, or at least 5 different methylation states at a respective CpG site (e.g., aligned to a reference genome) is retained. As another example, a first nucleic acid methylation fragment having the same methylation state vector (e.g., methylation pattern) but different corresponding genomic start and end positions as a second nucleic acid methylation fragment is also retained.

The filtering can remove assay artifacts in the plurality of nucleic acid methylation fragments. The removal of assay artifacts can comprise removing sequence reads obtained from sequenced hybridization probes and/or sequence reads obtained from sequences that failed to undergo conversion during bisulfite conversion. The filtering can remove contaminants (e.g., due to sequencing, nucleic acid isolation, and/or sample preparation).

The filtering can remove a subset of methylation fragments from the plurality of methylation fragments based on mutual information filtering of the respective methylation fragments against the cancer state across the plurality of training subjects. For example, mutual information can provide a measure of the mutual dependence between two conditions of interest sampled simultaneously. Mutual information can be determined by selecting an independent set of CpG sites (e.g., within all or a portion of a nucleic acid methylation fragment) from one or more datasets and comparing the probability of the methylation states for the set of CpG sites between two sample groups (e.g., subsets and/or groups of genotypic datasets, biological samples, and/or subjects). A mutual information score can denote the probability of the methylation pattern for a first condition versus a second condition at the respective region in the respective frame of the sliding window, thus indicating the discriminative power of the respective region. A mutual information score can be similarly calculated for each region in each frame of the sliding window as it progresses across the selected sets of CpG sites and/or the selected genomic regions. Further details regarding mutual information filtering are disclosed in U.S. patent application Ser. No. 17/119,606, titled "Cancer Classification using Patch Convolutional Neural Networks," filed Dec. 11, 2020, which is hereby incorporated herein by reference in its entirety.

II.C.II. Hypermethylated Fragments and Hypomethylated Fragments

In some embodiments, the analytics system determines anomalous fragments as fragments with over a threshold number of CpG sites and either with over a threshold percentage of the CpG sites methylated or with over a threshold percentage of CpG sites unmethylated; the analytics system identifies such fragments as hypermethylated fragments or hypomethylated fragments. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

II.D. Example Analytics System

Figure 6A:
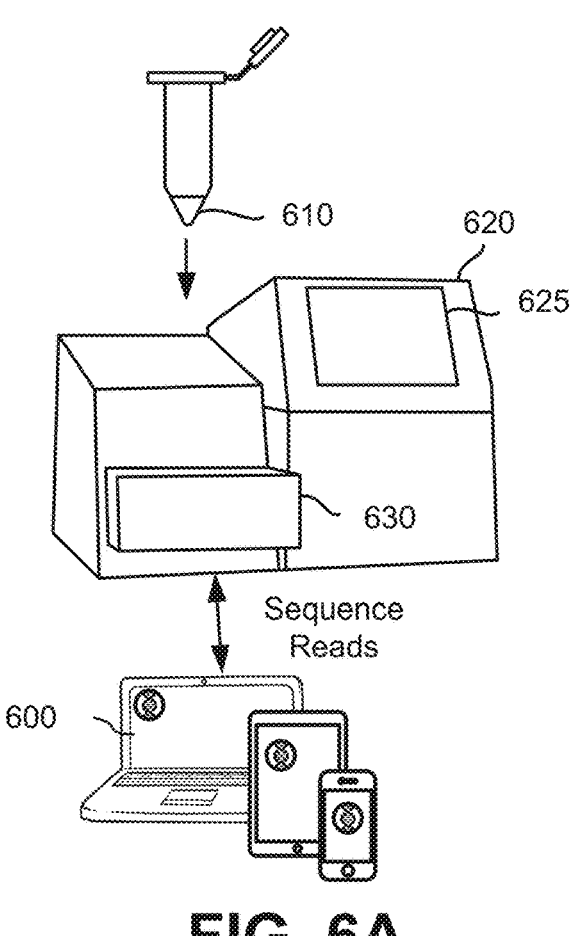
FIG. 6A illustrates an exemplary flowchart of devices for sequencing nucleic acid samples according to one or more embodiments.

FIG. 6A is an exemplary flowchart of devices for sequencing nucleic acid samples according to one or more embodiments. This illustrative flowchart includes devices such as a sequencer 620 and an analytics system 600. The sequencer 620 and the analytics system 600 may work in tandem to perform one or more steps in the processes 300 of FIG. 3A, 400 of FIG. 4A, 420 of FIG. 4B, and other processes described herein.

In various embodiments, the sequencer 620 receives an enriched nucleic acid sample 610. As shown in FIG. 6A, the sequencer 620 can include a graphical user interface 625 that enables user interactions with particular tasks (e.g., initiate sequencing or terminate sequencing) as well as one more loading stations 630 for loading a sequencing cartridge including the enriched fragment samples and/or for loading necessary buffers for performing the sequencing assays. Therefore, once a user of the sequencer 620 has provided the necessary reagents and sequencing cartridge to the loading station 630 of the sequencer 620, the user can initiate sequencing by interacting with the graphical user interface 625 of the sequencer 620. Once initiated, the sequencer 620 performs the sequencing and outputs the sequence reads of the enriched fragments from the nucleic acid sample 610.

In some embodiments, the sequencer 620 is communicatively coupled with the analytics system 600. The analytics system 600 includes some number of computing devices used for processing the sequence reads for various applications such as assessing methylation status at one or more CpG sites, variant calling or quality control. The sequencer 620 may provide the sequence reads in a BAM file format to the analytics system 600. The analytics system 600 can be communicatively coupled to the sequencer 620 through a wireless, wired, or a combination of wireless and wired communication technologies. Generally, the analytics system 600 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information, e.g., via step 340 of the process 300 in FIG. 3A. Alignment position may generally describe a beginning position and an end position of a region in the reference genome that corresponds to a beginning nucleotide base and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 600 may label a sequence read with one or more genes that align to the sequence read. In one embodiment, fragment length (or size) is determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome can represent the likely location within the reference genome to which the nucleic acid fragment corresponds. An output file having SAM (sequence alignment map) format or BAM (binary) format may be generated and output for further analysis.

Figure 6B:
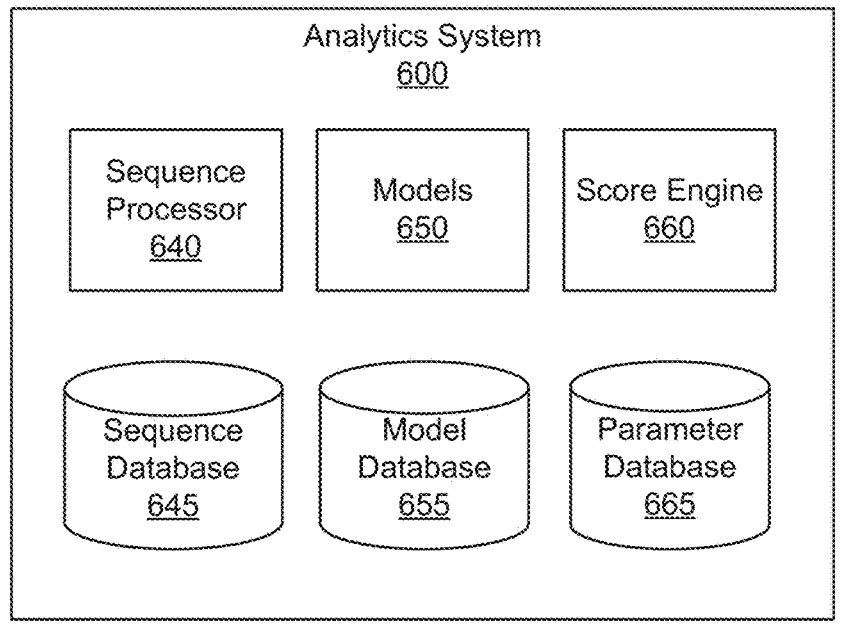
FIG. 6B is an exemplary block diagram of an analytics system, according to one or more embodiments.

Referring now to FIG. 6B, FIG. 6B is a block diagram of an analytics system 600 for processing DNA samples according to one embodiment. The analytics system implements one or more computing devices for use in analyzing DNA samples. The analytics system 600 includes a sequence processor 640, sequence database 645, model database 655, models 650, parameter database 665, and score engine 660. In some embodiments, the analytics system 600 performs some or all of the processes 300 of FIG. 3A and 400 of FIG. 4A.

The sequence processor 640 generates methylation state vectors for fragments from a sample. At each CpG site on a fragment, the sequence processor 640 generates a methylation state vector for each fragment specifying a location of the fragment in the reference genome, a number of CpG sites in the fragment, and the methylation state of each CpG site in the fragment whether methylated, unmethylated, or indeterminate via the process 300 of FIG. 3A. The sequence processor 640 may store methylation state vectors for fragments in the sequence database 645. Data in the sequence database 645 may be organized such that the methylation state vectors from a sample are associated to one another.

Further, multiple different models 650 may be stored in the model database 655 or retrieved for use with test samples. In one example, a model is a trained cancer classifier for determining a cancer prediction for a test sample using a feature vector derived from anomalous fragments. The training and use of the cancer classifier will be further discussed in conjunction with Section III. Cancer Classifier for Determining Cancer. The analytics system 600 may train the one or more models 650 and store various trained parameters in the parameter database 665. The analytics system 600 stores the models 650 along with functions in the model database 655.

During inference, the score engine 660 uses the one or more models 650 to return outputs. The score engine 660 accesses the models 650 in the model database 655 along with trained parameters from the parameter database 665. According to each model, the score engine receives an appropriate input for the model and calculates an output based on the received input, the parameters, and a function of each model relating the input and the output. In some use cases, the score engine 660 further calculates metrics correlating to a confidence in the calculated outputs from the model. In other use cases, the score engine 660 calculates other intermediary values for use in the model.

III. Cancer Classifier for Determining Cancer

III.A. Overview

The cancer classifier can be trained to receive a feature vector for a test sample and determine whether the test sample is from a test subject that has cancer or, more specifically, a particular cancer type. The cancer classifier can comprise a plurality of classification parameters and a function representing a relation between the feature vector as input and the cancer prediction as output determined by the function operating on the input feature vector with the classification parameters. In some embodiments, the feature vectors input into the cancer classifier are based on set of anomalous fragments determined from the test sample. The anomalous fragments may be determined via the process 420 in FIG. 4B, or more specifically hypermethylated and hypomethylated fragments as determined via the step 470 of the process 420, or anomalous fragments determined according to some other process. Prior to deployment of the cancer classifier, the analytics system can train the cancer classifier.

III.B. Training of Cancer Classifier

FIG. 5A is a flowchart describing a process 500 of training a cancer classifier, according to an embodiment. The analytics system obtains 510 a plurality of training samples each having a set of anomalous fragments and a label of a cancer type. The plurality of training samples can include any combination of samples from healthy individuals with a general label of "non-cancer," samples from subjects with a general label of "cancer" or a specific label (e.g., "breast cancer," "lung cancer," etc.). The training samples from subjects for one cancer type may be termed a cohort for that cancer type or a cancer type cohort.

The analytics system determines 520, for each training sample, a feature vector based on the set of anomalous fragments of the training sample. The analytics system can calculate an anomaly score for each CpG site in an initial set of CpG sites. The initial set of CpG sites may be all CpG sites in the human genome or some portion thereof—which may be on the order of $10^4$, $10^5$, $10^6$, $10^7$, $10^8$, etc. In one embodiment, the analytics system defines the anomaly score for the feature vector with a binary scoring based on whether there is an anomalous fragment in the set of anomalous fragments that encompasses the CpG site. In another embodiment, the analytics system defines the anomaly score based on a count of anomalous fragments overlapping the CpG site. In one example, the analytics system may use a trinary scoring assigning a first score for lack of presence of anomalous fragments, a second score for presence of a few anomalous fragments, and a third score for presence of more than a few anomalous fragments. For example, the analytics system counts 5 anomalous fragments in a sample that overlap the CpG site and calculates an anomaly score based on the count of 5.

Once all anomaly scores are determined for a training sample, the analytics system can determine the feature vector as a vector of elements including, for each element, one of the anomaly scores associated with one of the CpG sites in an initial set. The analytics system can normalize the anomaly scores of the feature vector based on a coverage of the sample. Here, coverage can refer to a median or average sequencing depth over all CpG sites covered by the initial set of CpG sites used in the classifier, or based on the set of anomalous fragments for a given training sample.

Figure 5B:
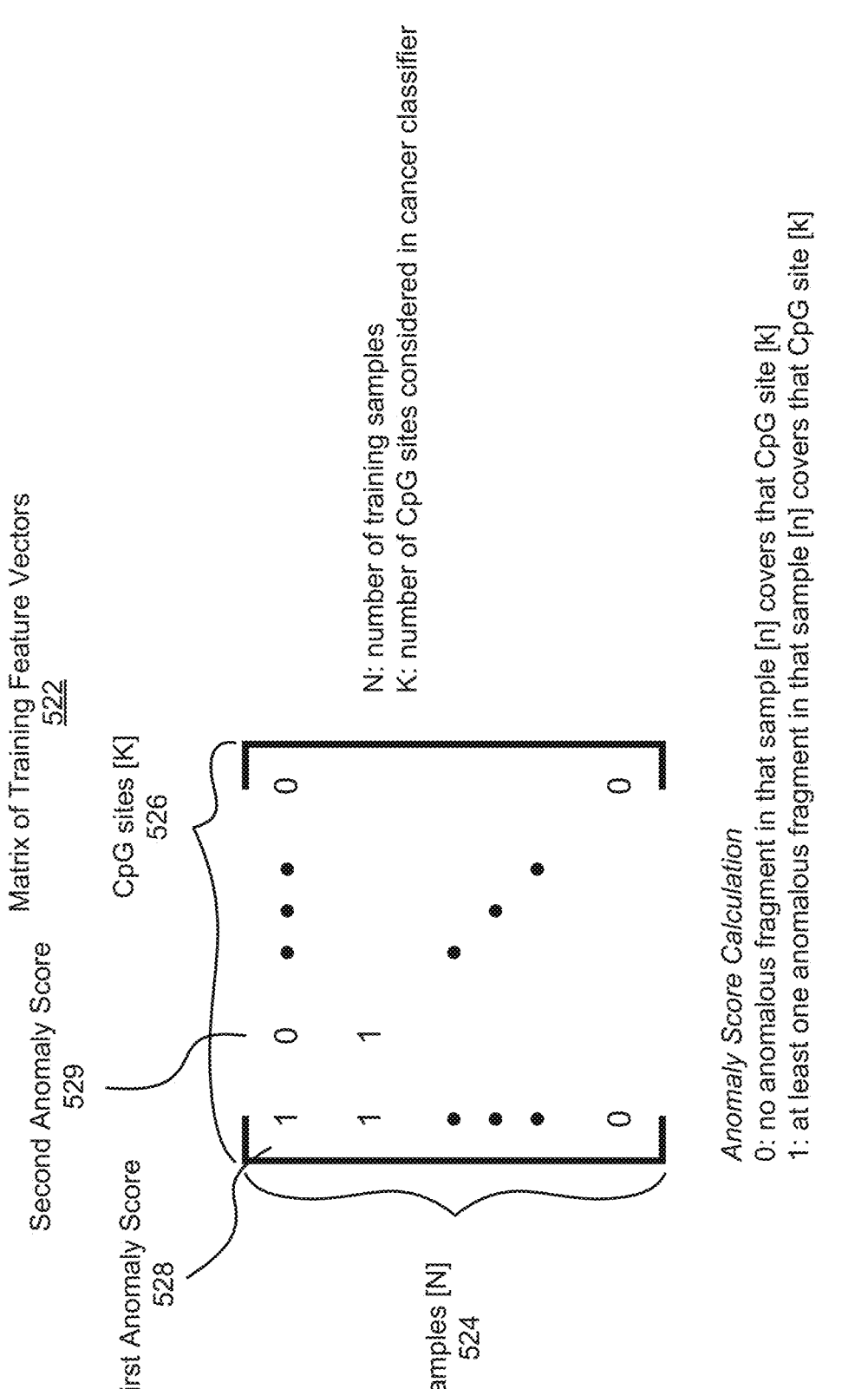
FIG. 5B illustrates an example generation of feature vectors used for training the cancer classifier, according to one or more embodiments.

As an example, reference is now made to FIG. 5B illustrating a matrix of training feature vectors 522. In this example, the analytics system has identified CpG sites [K] 526 for consideration in generating feature vectors for the cancer classifier. The analytics system selects training samples [N] 524. The analytics system determines a first anomaly score 528 for a first arbitrary CpG site [k1] to be used in the feature vector for a training sample [n1]. The analytics system checks each anomalous fragment in the set of anomalous fragments. If the analytics system identifies at least one anomalous fragment that includes the first CpG site, then the analytics system determines the first anomaly score 528 for the first CpG site as 1, as illustrated in FIG. 5B. Considering a second arbitrary CpG site [k2], the analytics system similarly checks the set of anomalous fragments for at least one that includes the second CpG site [k2]. If the analytics system does not find any such anomalous fragment that includes the second CpG site, the analytics system determines a second anomaly score 529 for the second CpG site [k2] to be 0, as illustrated in FIG. 5B. Once the analytics system determines all the anomaly scores for the initial set of CpG sites, the analytics system determines the feature vector for the first training sample [n1] including the anomaly scores with the feature vector including the first anomaly score 528 of 1 for the first CpG site [k1] and the second anomaly score 529 of 0 for the second CpG site [k2] and subsequent anomaly scores, thus forming a feature vector [1, 0, . . . ].

Additional approaches to featurization of a sample can be found in: U.S. application Ser. No. 15/931,022 entitled "Model-Based Featurization and Classification;" U.S. application Ser. No. 16/579,805 entitled "Mixture Model for Targeted Sequencing;" U.S. application Ser. No. 16/352,602 entitled "Anomalous Fragment Detection and Classification; " and U.S. application Ser. No. 16/723,716 entitled "Source of Origin Deconvolution Based on Methylation Fragments in Cell-Free DNA Samples;" all of which are incorporated by reference in their entirety.

The analytics system may further limit the CpG sites considered for use in the cancer classifier. The analytics system computes 530, for each CpG site in the initial set of CpG sites, an information gain based on the feature vectors of the training samples. From step 520, each training sample has a feature vector that may contain an anomaly score for all CpG sites in the initial set of CpG sites which could include up to all CpG sites in the human genome. However, some CpG sites in the initial set of CpG sites may not be as informative as others in distinguishing between cancer types, or may be duplicative with other CpG sites.

In one embodiment, the analytics system computes 530 an information gain for each cancer type and for each CpG site in the initial set to determine whether to include that CpG site in the classifier. The information gain is computed for training samples with a given cancer type compared to all other samples. For example, two random variables 'anomalous fragment' ('AF') and 'cancer type' ('CT') are used. In one embodiment, AF is a binary variable indicating whether there is an anomalous fragment overlapping a given CpG site in a given sample as determined for the anomaly score/feature vector above. CT is a random variable indicating whether the cancer is of a particular type. The analytics system computes the mutual information with respect to CT given AF. That is, how many bits of information about the cancer type are gained if it is known whether there is an anomalous fragment overlapping a particular CpG site. In practice, for a first cancer type, the analytics system computes pairwise mutual information gain against each other cancer type and sums the mutual information gain across all the other cancer types.

For a given cancer type, the analytics system can use this information to rank CpG sites based on how cancer specific they are. This procedure can be repeated for all cancer types under consideration. If a particular region is commonly anomalously methylated in training samples of a given cancer but not in training samples of other cancer types or in healthy training samples, then CpG sites overlapped by those anomalous fragments can have high information gains for the given cancer type. The ranked CpG sites for each cancer type can be greedily added (selected) 540 to a selected set of CpG sites based on their rank for use in the cancer classifier.

In additional embodiments, the analytics system may consider other selection criteria for selecting informative CpG sites to be used in the cancer classifier. One selection criterion may be that the selected CpG sites are above a threshold separation from other selected CpG sites. For example, the selected CpG sites are to be over a threshold number of base pairs away from any other selected CpG site (e.g., 100 base pairs), such that CpG sites that are within the threshold separation are not both selected for consideration in the cancer classifier.

In one embodiment, according to the selected set of CpG sites from the initial set, the analytics system may modify 550 the feature vectors of the training samples as needed. For example, the analytics system may truncate feature vectors to remove anomaly scores corresponding to CpG sites not in the selected set of CpG sites.

With the feature vectors of the training samples, the analytics system may train the cancer classifier in any of a number of ways. The feature vectors may correspond to the initial set of CpG sites from step 520 or to the selected set of CpG sites from step 550. In one embodiment, the analytics system trains 560 a binary cancer classifier to distinguish between cancer and non-cancer based on the feature vectors of the training samples. In this manner, the analytics system uses training samples that include both non-cancer samples from healthy individuals and cancer samples from subjects. Each training sample can have one of the two labels "cancer" or "non-cancer." In this embodiment, the classifier outputs a cancer prediction indicating the likelihood of the presence or absence of cancer.

In another embodiment, the analytics system trains 570 a multiclass cancer classifier to distinguish between many cancer types (also referred to as tissue of origin (TOO) labels). Cancer types can include one or more cancers and may include a non-cancer type (may also include any additional other diseases or genetic disorders, etc.). To do so, the analytics system can use the cancer type cohorts and may also include or not include a non-cancer type cohort. In this multi-cancer embodiment, the cancer classifier is trained to determine a cancer prediction (or, more specifically, a TOO prediction) that comprises a prediction value for each of the cancer types being classified for. The prediction values may correspond to a likelihood that a given training sample (and during inference, a test sample) has each of the cancer types. In one implementation, the prediction values are scored between 0 and 100, wherein the cumulation of the prediction values equals 100. For example, the cancer classifier returns a cancer prediction including a prediction value for breast cancer, lung cancer, and non-cancer. For example, the classifier can return a cancer prediction that a test sample has 65% likelihood of breast cancer, 25% likelihood of lung cancer, and 10% likelihood of non-cancer. The analytics system may further evaluate the prediction values to generate a prediction of a presence of one or more cancers in the sample, also may be referred to as a TOO prediction indicating one or more TOO labels, e.g., a first TOO label with the highest prediction value, a second TOO label with the second highest prediction value, etc. Continuing with the example above and given the percentages, in this example the system may determine that the sample has breast cancer given that breast cancer has the highest likelihood.

In both embodiments, the analytics system trains the cancer classifier by inputting sets of training samples with their feature vectors into the cancer classifier and adjusting classification parameters so that a function of the classifier accurately relates the training feature vectors to their corresponding label. The analytics system may group the training samples into sets of one or more training samples for iterative batch training of the cancer classifier. In one embodiment, the training process includes initializing parameters of the cancer classifier (e.g., neural network model). The batch of training samples (e.g., feature vectors) are input to the cancer classifier to generate estimated outputs. A loss function (e.g., L2 norm, L1 norm, L-infinity norm) is computed that indicates a difference between the estimated outputs and the known labels for the training samples. Terms obtained from the loss function are back-propagated to update the parameters. This process is repeated until some convergence criteria is reached. After inputting all sets of training samples including their training feature vectors and adjusting the classification parameters, the cancer classifier can be sufficiently trained to label test samples according to their feature vector within some margin of error.

The analytics system may train the cancer classifier according to any one of a number of methods, including backpropagation via gradient descent, and the like. As an example, the binary (or multi-class) cancer classifier may be a L2-regularized logistic regression classifier that is trained using a log-loss function. As another example, the multi-cancer classifier may be a multinomial logistic regression. In practice either type of cancer classifier may be trained using other techniques. These techniques are numerous including potential use of kernel methods, random forest classifier, a mixture model, an autoencoder model, machine learning algorithms such as multilayer neural networks, etc.

The classifier can include a logistic regression algorithm, a neural network algorithm (e.g., artificial neural network, deep neural network), a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

III.C. Deployment of Cancer Classifier

During use of the cancer classifier, the analytics system can obtain a test sample from a subject of unknown cancer type. The analytics system may process the test sample comprised of DNA molecules with any combination of the processes 300, 400, and 420 to achieve a set of anomalous fragments. The analytics system can determine a test feature vector for use by the cancer classifier according to similar principles discussed in the process 500. The analytics system can calculate an anomaly score for each CpG site in a plurality of CpG sites in use by the cancer classifier. For example, the cancer classifier receives as input feature vectors inclusive of anomaly scores for 1,000 selected CpG sites. The analytics system can thus determine a test feature vector inclusive of anomaly scores for the 1,000 selected CpG sites based on the set of anomalous fragments. The analytics system can calculate the anomaly scores in the same manner as the training samples. In some embodiments, the analytics system defines the anomaly score as a binary score based on whether there is a hypermethylated or hypomethylated fragment in the set of anomalous fragments that encompasses the CpG site.

The analytics system can then input the test feature vector into the cancer classifier. The function of the cancer classifier can then generate a cancer prediction based on the classification parameters trained in the process 500 and the test feature vector. In the first manner, the cancer prediction can be binary and selected from a group consisting of "cancer" or non-cancer;" in the second manner, the cancer prediction is selected from a group of many cancer types and "non-cancer." In additional embodiments, the cancer prediction has predicted values for each of the many cancer types. Moreover, the analytics system may determine that the test sample is most likely to be of one of the cancer types. Following the example above with the cancer prediction for a test sample as 65% likelihood of breast cancer, 25% likelihood of lung cancer, and 10% likelihood of non-cancer, the analytics system may determine that the test sample is most likely to have breast cancer. In another example, where the cancer prediction is binary as 60% likelihood of non-cancer and 40% likelihood of cancer, the analytics system determines that the test sample is most likely not to have cancer. In additional embodiments, the cancer prediction with the highest likelihood may still be compared against a threshold (e.g., 40%, 50%, 60%, 70%) in order to call the test subject as having that cancer type. If the cancer prediction with the highest likelihood does not surpass that threshold, the analytics system may return an inconclusive result.

In additional embodiments, the analytics system chains a cancer classifier trained in step 560 of the process 500 with another cancer classifier trained in step 570 or the process 500. The analytics system can input the test feature vector into the cancer classifier trained as a binary classifier in step 560 of the process 500. The analytics system can receive an output of a cancer prediction. The cancer prediction may be binary as to whether the test subject likely has or likely does not have cancer. In other implementations, the cancer prediction includes prediction values that describe likelihood of cancer and likelihood of non-cancer. For example, the cancer prediction has a cancer prediction value of 85% and the non-cancer prediction value of 15%. The analytics system may determine the test subject to likely have cancer. Once the analytics system determines a test subject is likely to have cancer, the analytics system may input the test feature vector into a multiclass cancer classifier trained to distinguish between different cancer types. The multiclass cancer classifier can receive the test feature vector and returns a cancer prediction of a cancer type of the plurality of cancer types. For example, the multiclass cancer classifier provides a cancer prediction specifying that the test subject is most likely to have ovarian cancer. In another implementation, the multiclass cancer classifier provides a prediction value for each cancer type of the plurality of cancer types. For example, a cancer prediction may include a breast cancer type prediction value of 40%, a colorectal cancer type prediction value of 15%, and a liver cancer prediction value of 45%.

According to generalized embodiment of binary cancer classification, the analytics system can determine a cancer score for a test sample based on the test sample's sequencing data (e.g., methylation sequencing data, SNP sequencing data, other DNA sequencing data, RNA sequencing data, etc.). The analytics system can compare the cancer score for the test sample against a binary threshold cutoff for predicting whether the test sample likely has cancer. The binary threshold cutoff can be tuned using TOO thresholding based on one or more TOO subtype classes. The analytics system may further generate a feature vector for the test sample for use in the multiclass cancer classifier to determine a cancer prediction indicating one or more likely cancer types.

The classifier may be used to determine the disease state of a test subject, e.g., a subject whose disease status is unknown. The method can include obtaining a test genomic data construct (e.g., single time point test data), in electronic form, that includes a value for each genomic characteristic in the plurality of genomic characteristics of a corresponding plurality of nucleic acid fragments in a biological sample obtained from a test subject. The method can then include applying the test genomic data construct to the test classifier to thereby determine the state of the disease condition in the test subject. The test subject may not be previously diagnosed with the disease condition.

The classifier can be a temporal classifier that uses at least (i) a first test genomic data construct generated from a first biological sample acquired from a test subject at a first point in time, and (ii) a second test genomic data construct generated from a second biological sample acquired from a test subject at a second point in time.

The trained classifier can be used to determine the disease state of a test subject, e.g., a subject whose disease status is unknown. In this case, the method can include obtaining a test time-series data set, in electronic form, for a test subject, where the test time-series data set includes, for each respective time point in a plurality of time points, a corresponding test genotypic data construct including values for the plurality of genotypic characteristics of a corresponding plurality of nucleic acid fragments in a corresponding biological sample obtained from the test subject at the respective time point, and for each respective pair of consecutive time points in the plurality of time points, an indication of the length of time between the respective pair of consecutive time points. The method can then include applying the test genotypic data construct to the test classifier to thereby determine the state of the disease condition in the test subject. The test subject may not be previously diagnosed with the disease condition.

IV. Applications

In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a probability score (e.g., from 0 to 100) describing a likelihood that a test feature vector is from a subject with cancer. In some embodiments, the probability score is compared to a threshold probability to determine whether or not the subject has cancer. In other embodiments, the likelihood or probability score can be assessed at multiple different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the probability score exceeds a threshold, a physician can prescribe an appropriate treatment.

IV.A. Early Detection of Cancer

In some embodiments, the methods and/or classifier of the present invention are used to detect the presence or absence of cancer in a subject suspected of having cancer. For example, a classifier (e.g., as described above in Section III and exampled in Section V) can be used to determine a cancer prediction describing a likelihood that a test feature vector is from a subject that has cancer.

In one embodiment, a cancer prediction is a likelihood (e.g., scored between 0 and 100) for whether the test sample has cancer (i.e. binary classification). Thus, the analytics system may determine a threshold for determining whether a test subject has cancer. For example, a cancer prediction of greater than or equal to 60 can indicate that the subject has cancer. In still other embodiments, a cancer prediction greater than or equal to 65, greater than or equal to 70, greater than or equal to 75, greater than or equal to 80, greater than or equal to 85, greater than or equal to 90, or greater than or equal to 95 indicates that the subject has cancer. In other embodiments, the cancer prediction can indicate the severity of disease. For example, a cancer prediction of 80 may indicate a more severe form, or later stage, of cancer compared to a cancer prediction below 80 (e.g., a probability score of 70). Similarly, an increase in the cancer prediction over time (e.g., determined by classifying test feature vectors from multiple samples from the same subject taken at two or more time points) can indicate disease progression or a decrease in the cancer prediction over time can indicate successful treatment.

In another embodiment, a cancer prediction comprises many prediction values, wherein each of a plurality of cancer types being classified (i.e. multiclass classification) for has a prediction value (e.g., scored between 0 and 100). The prediction values may correspond to a likelihood that a given training sample (and during inference, training sample) has each of the cancer types. The analytics system may identify the cancer type that has the highest prediction value and indicate that the test subject likely has that cancer type. In other embodiments, the analytics system further compares the highest prediction value to a threshold value (e.g., 50, 55, 60, 65, 70, 75, 80, 85, etc.) to determine that the test subject likely has that cancer type. In other embodiments, a prediction value can also indicate the severity of disease. For example, a prediction value greater than 80 may indicate a more severe form, or later stage, of cancer compared to a prediction value of 60. Similarly, an increase in the prediction value over time (e.g., determined by classifying test feature vectors from multiple samples from the same subject taken at two or more time points) can indicate disease progression or a decrease in the prediction value over time can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, ten or more, fifteen or more, or twenty or more different types of cancer.

Examples of cancers that can be detected using the methods, systems and classifiers of the present invention include carcinoma, lymphoma, blastoma, sarcoma, and leukemia or lymphoid malignancies. More particular examples of such cancers include, but are not limited to, squamous cell cancer (e.g., epithelial squamous cell cancer), skin carcinoma, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), cervical cancer, ovarian cancer (e.g., high grade serous ovarian carcinoma), liver cancer (e.g., hepatocellular carcinoma (HCC)), hepatoma, hepatic carcinoma, bladder cancer (e.g., urothelial bladder cancer), testicular (germ cell tumor) cancer, breast cancer (e.g., HER2 positive, HER2 negative, and triple negative breast cancer), brain cancer (e.g., astrocytoma, glioma (e.g., glioblastoma)), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, anal carcinoma, penile carcinoma, head and neck cancer, esophageal carcinoma, and nasopharyngeal carcinoma (NPC). Additional examples of cancers include, without limitation, retinoblastoma, thecoma, arrhenoblastoma, hematological malignancies, including but not limited to non-Hodgkin's lymphoma (NHL), multiple myeloma and acute hematological malignancies, endometriosis, fibrosarcoma, choriocarcinoma, laryngeal carcinomas, Kaposi's sarcoma, Schwannoma, oligodendroglioma, neuroblastomas, rhabdomyosarcoma, osteogenic sarcoma, leiomyosarcoma, and urinary tract carcinomas.

In some embodiments, the cancer is one or more of anorectal cancer, bladder cancer, breast cancer, cervical cancer, colorectal cancer, esophageal cancer, gastric cancer, head & neck cancer, hepatobiliary cancer, leukemia, lung cancer, lymphoma, melanoma, multiple myeloma, ovarian cancer, pancreatic cancer, prostate cancer, renal cancer, thyroid cancer, uterine cancer, or any combination thereof.

In some embodiments, the one or more cancer can be a "high-signal" cancer (defined as cancers with greater than 50% 5-year cancer-specific mortality), such as anorectal, colorectal, esophageal, head & neck, hepatobiliary, lung, ovarian, and pancreatic cancers, as well as lymphoma and multiple myeloma. High-signal cancers tend to be more aggressive and typically have an above-average cell-free nucleic acid concentration in test samples obtained from a patient.

IV.B. Cancer and Treatment Monitoring

In some embodiments, the cancer prediction can be assessed at multiple different time points (e.g., or before or after treatment) to monitor disease progression or to monitor treatment effectiveness (e.g., therapeutic efficacy). For example, the present invention include methods that involve obtaining a first sample (e.g., a first plasma cfDNA sample) from a cancer patient at a first time point, determining a first cancer prediction therefrom (as described herein), obtaining a second test sample (e.g., a second plasma cfDNA sample) from the cancer patient at a second time point, and determining a second cancer prediction therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the classifier is utilized to monitor the effectiveness of the treatment. For example, if the second cancer prediction decreases compared to the first cancer prediction, then the treatment is considered to have been successful. However, if the second cancer prediction increases compared to the first cancer prediction, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., after a resection surgery or a therapeutic intervention). In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

Those of skill in the art will readily appreciate that test samples can be obtained from a cancer patient over any desired set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 50 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 5 months, at least once every 6 months, at least once a year, at least once every 2 years, at least once every 3 years, at least once every 4 years, or at least once every 5 years.

IV.C. Treatment

In still another embodiment, the cancer prediction can be used to make or influence a clinical decision (e.g., diagnosis of cancer, treatment selection, assessment of treatment effectiveness, etc.). For example, in one embodiment, if the cancer prediction (e.g., for cancer or for a particular cancer type) exceeds a threshold, a physician can prescribe an appropriate treatment (e.g., a resection surgery, radiation therapy, chemotherapy, and/or immunotherapy).

A classifier (as described herein) can be used to determine a cancer prediction that a sample feature vector is from a subject that has cancer. In one embodiment, an appropriate treatment (e.g., resection surgery or therapeutic) is prescribed when the cancer prediction exceeds a threshold. For example, in one embodiment, if the cancer prediction is greater than or equal to 60 one or more appropriate treatments are prescribed. In another embodiment, if the cancer prediction is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, the cancer prediction can indicate the severity of disease. An appropriate treatment matching the severity of the disease may then be prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HIDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

V. Example Results

V.A. Sample Collection and Processing

Study design and samples: CCGA (NCT02889978) is a prospective, multi-center, case-control, observational study with longitudinal follow-up. De-identified biospecimens were collected from approximately 15,000 participants from 342 sites. Samples were divided into training (1,785) and test (1,015) sets; samples were selected to ensure a prespecified distribution of cancer types and non-cancers across sites in each cohort, and cancer and non-cancer samples were frequency age-matched by gender.

Whole-genome bisulfite sequencing: cfDNA was isolated from plasma, and whole-genome bisulfite sequencing (WGBS; 30× depth) was employed for analysis of cfDNA. cfDNA was extracted from two tubes of plasma (up to a combined volume of 10 ml) per patient using a modified QIAamp Circulating Nucleic Acid kit (Qiagen; Germantown, MD). Up to 75 ng of plasma cfDNA was subjected to bisulfite conversion using the EZ-96 DNA Methylation Kit (Zymo Research, D5003). Converted cfDNA was used to prepare dual indexed sequencing libraries using Accel-NGS Methyl-Seq DNA library preparation kits (Swift BioSciences; Ann Arbor, MI) and constructed libraries were quantified using KAPA Library Quantification Kit for Illumina Platforms (Kapa Biosystems; Wilmington, MA). Four libraries along with 10% PhiX v3 library (Illumina, FC-110-3001) were pooled and clustered on an Illumina NovaSeq 7000 S2 flow cell followed by 150-bp paired-end sequencing (30×).

For each sample, the WGBS fragment set was reduced to a small subset of fragments having an anomalous methylation pattern. Additionally, hyper or hypomethylated cfDNA fragments were selected. cfDNA fragments selected for having an anomalous methylation pattern and being hyper or hypermethylated, i.e., UFXM. Fragments occurring at high frequency in individuals without cancer, or that have unstable methylation, are unlikely to produce highly discriminatory features for classification of cancer status. We therefore produced a statistical model and a data structure of typical fragments using an independent reference set of 108 non-smoking participants without cancer (age: 58±14 years, 79 [73%] women) (i.e., a reference genome) from the CCGA study. These samples were used to train a Markov-chain model (order 3) estimating the likelihood of a given sequence of CpG methylation statuses within a fragment as described above in Section II.C. This model was demonstrated to be calibrated within the normal fragment range (p-value>0.001) and was used to reject fragments with a p-value from the Markov model as >=0.001 as insufficiently unusual.

As described above, further data reduction steps selected only fragments with at least 5 CpGs covered, and average methylation either >0.9 (hyper methylated) or <0.1 (hypomethylated). This procedure resulted in a median (range) of 2,800 (1,500-12,000) UFXM fragments for participants without cancer in training, and a median (range) of 3,000 (1,200-420,000) UFXM fragments for participants with cancer in training. As this data reduction procedure only used reference set data, this stage was only required to be applied to each sample once.

V.B. Contamination Detection Results

Figure 7:
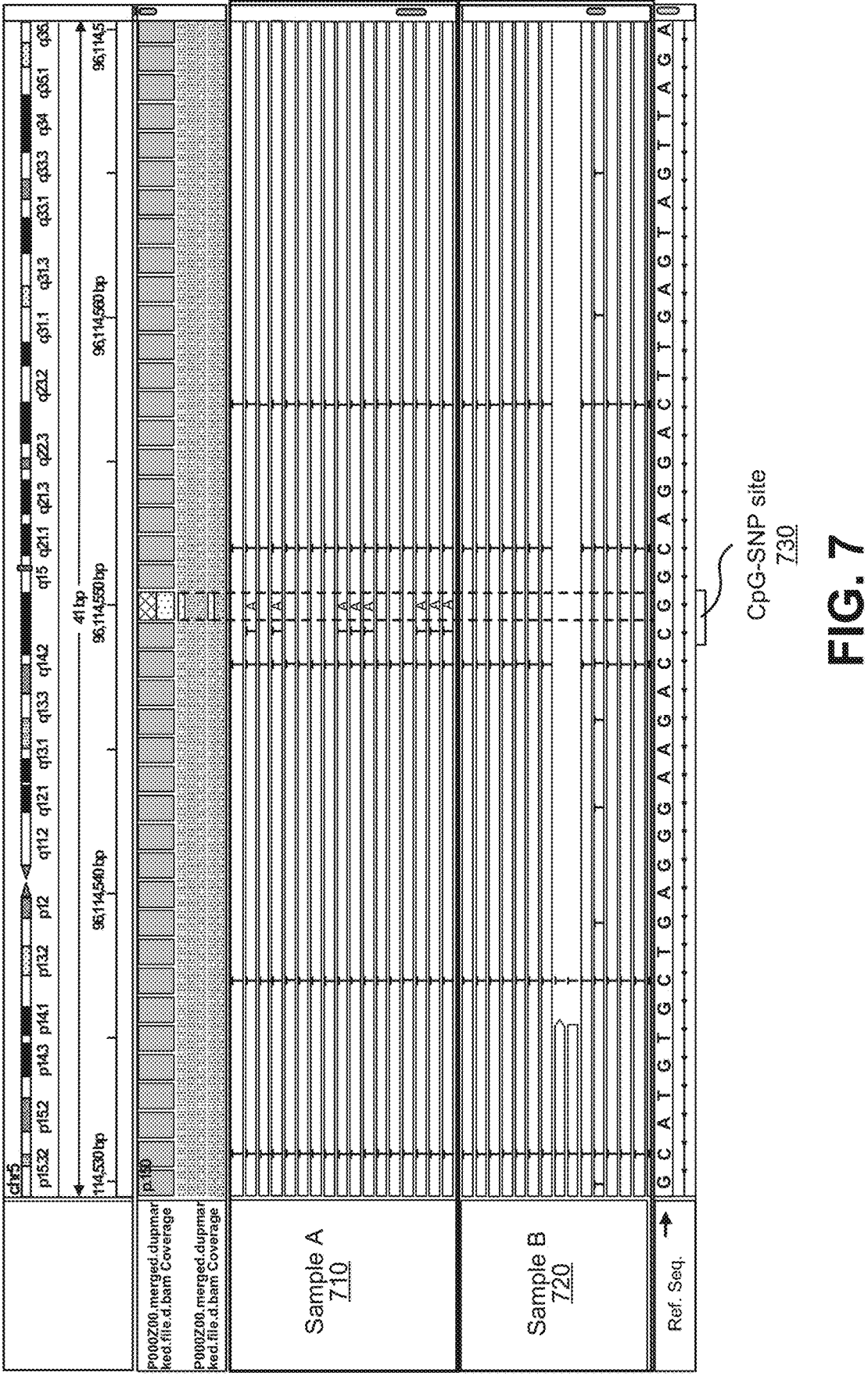
FIG. 7 illustrates a CpG-SNP site with Sample A as heterozygous and Sample B as homozygous absent the SNP, according to example results. Figure discloses SEQ ID NO: 4.

FIG. 7 illustrates a CpG-SNP site with Sample A 710 as heterozygous and Sample B 720 as homozygous absent the SNP, according to example results. The analytic system utilized contamination marker probes to identify contaminated fragments in the samples. The samples were prepared with bisulfite sequencing, e.g., as described and shown in FIGS. 3A & 3B. The bottom row identifies the reference sequence. The CpG-SNP site 730 is a subtractive CpG-SNP site wherein the SNP removes a CpG. Each row for a sample indicates a sequence read for a cfDNA fragment in the sample. As shown in the samples, a "T" on a fragment aligned over a "C" in the reference sequence indicates cytosines converted to uracil during the bisulfite sequencing process. In context of CpG sites, the T represents an unmethylated CpG site, whereas absent the "T" represents a methylated CpG site. Sample B 720 at the CpG-SNP site 730 has no fragment bearing a "T" aligned over the "C" in the reference sequence, thus Sample B 720 is homozygous for methylation at the CpG-SNP site 730. On the other hand, Sample A 710 is heterozygous at the CpG-SNP site 730. Here, the SNP alters the "G" to the "A" in the CpG. The SNP removes the existing CpG site, such that the cytosine is no longer methylated, thereby converting to uracil and sequenced as "T" in the bisulfite sequencing process. Approximately half of the fragments show absence of the SNP removing the CpG site and approximately half of the fragments show presence of the SNP removing the CpG site. Specifically, the fragments absent the SNP show methylation at the CpG site (akin to Sample B 720), but the fragments showing presence of the SNP comprise "T" and "A" aligned over the "C" and "G" in the reference sequence. If, for example, the analytics system were to identify a fragment in Sample B 720 that is homozygous for absent the SNP at the CpG-SNP site, then a fragment with the SNP present at the CpG-SNP site would be labeled to be a contamination fragment.

FIG. 8A illustrates a hybrid site as a double CpG-SNP site with Sample C 810 as homozygous absent two SNP's and Sample D 820 as homozygous present two SNP's, according to example results. The hybrid site comprises the first CpG-SNP site 830 and the second CpG-SNP site 840. The first CpG-SNP site 830 may exhibit a SNP altering the "C" to a "T", whereas the second CpG-SNP site 840 may exhibit a SNP altering the "G" to an "A". For Sample C 810, both SNPs are absent and the CpG sites are shown as always methylated, represented by the red blocks shaded as "Methylated." The forward strands are shown as gray reads shaded "Forward read" with the reverse strands shown as green reads shaded "Reverse read." On the reverse strands, the neighboring G bases (C on reverse strand) are shown as methylated as expected. For Sample D 820, both SNPs are present, removing both CpG sites. On forward strand gray reads, the first CpG-SNP site 830 is shown as an unmethylated "CG" (this is how the visualizer interprets a "TG"), followed by a "CA" for the second CpG-SNP site 840 (which is a CpG breaking double hit generated by the SNP since first C is normally always methylated, and A is a sequence variant). In total there are 3 hits (2 unmethylated "C"s and an "A"). On reverse strand green reads, a "TG" (sequence variant T plus unmethylated C as a G, which is a double hit) is observed for the first CpG-SNP site 830, plus an unmethylated G on the second CpG-SNP site 840. In total there are 3 hits (2 unmethylated "C"s and a "T"). In this hybrid site, the combined alternative variant observed (within 10 bps) uses 3 independent sequence changes to turn into the reference allele and vice versa, and importantly evidence is present on either strand increasing total coverage.

Figure 8B:
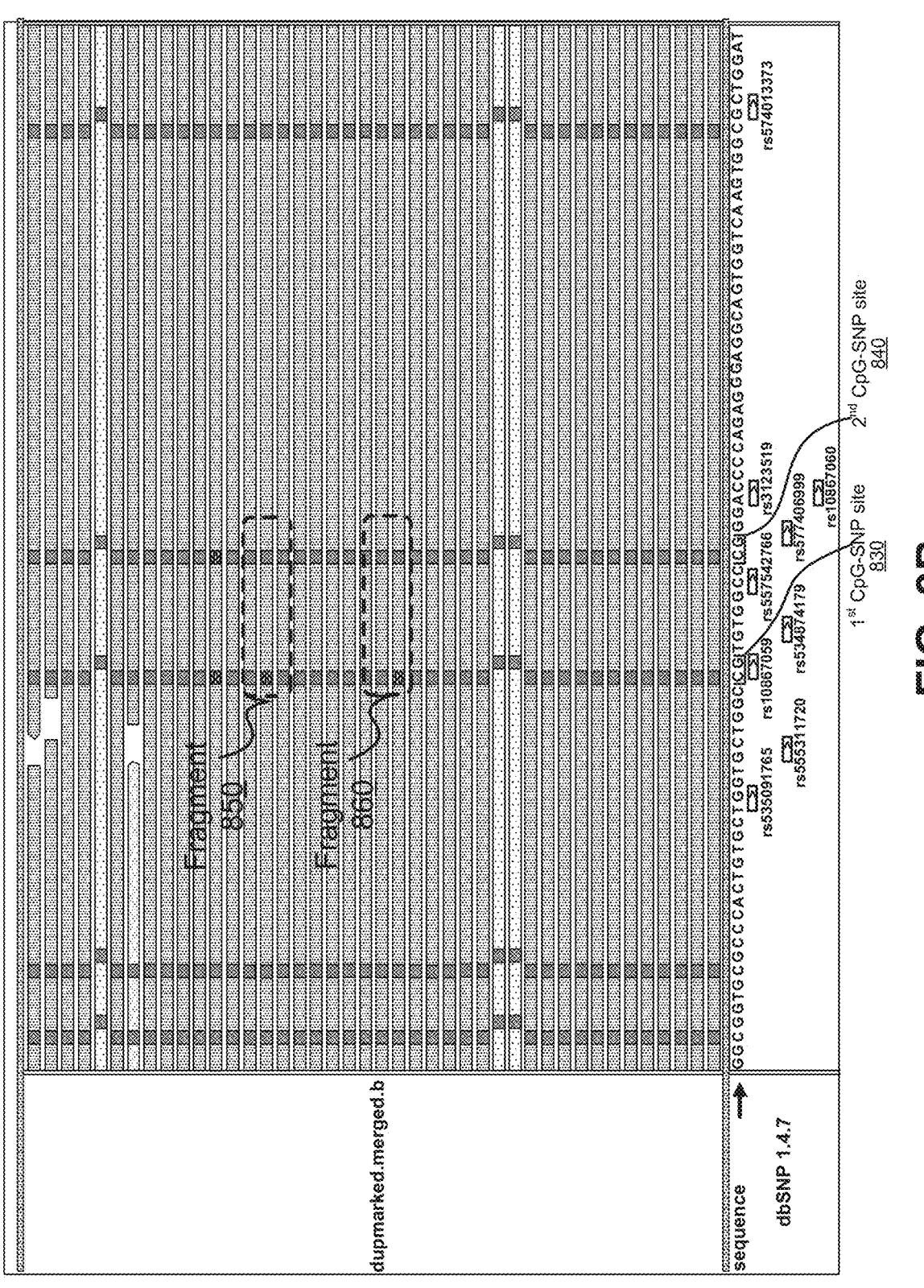
FIG. 8B illustrates contamination detection utilizing the hybrid site as the double CpG-SNP site of FIG. 8A, according to example results. Figure discloses SEQ ID NO: 9.

FIG. 8B illustrates contamination detection utilizing the hybrid site as the double CpG-SNP site of FIG. 8A, according to example results. The sequence reads for cfDNA fragments are shown for a third sample. In the third sample, a large majority of the sequence reads and fragments show absence of the two SNPs akin to Sample C 810, thus continued existence of the two CpG sites. One fragment shows two blue boxes shaded for "Unmethylated" indicating both CpG sites to be unmethylated, which may be due to sequencing error or naturally occurring unmethylation, etc. Two fragments, fragment 850 and fragment 860, both show presence of the two SNPs akin to Sample D 820. As such, for the two fragments, the first CpG-SNP site shows "TG", which the illustrator displays as an unmethylated "C" in the CpG site, and the second CpG-SNP site shows as "CA". Given that the large majority of the sample's fragments are homozygous for absence of the two SNPs at the double CpG-SNP site, the analytics system may determine or call fragments 850 and 860 as contamination fragments for having a different haplotype compared to the homozygous haplotype.

Figure 9A:
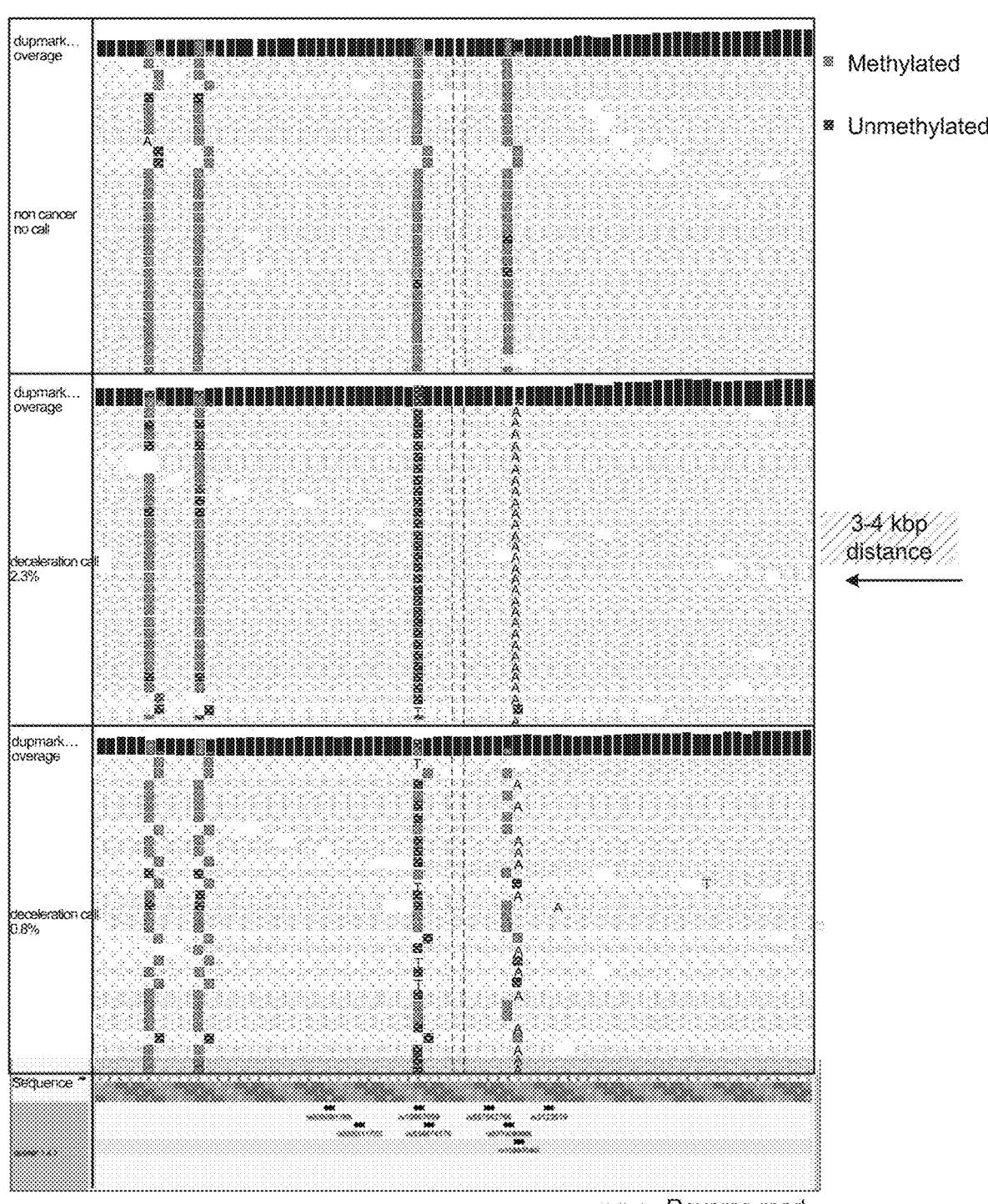
FIG. 9A further illustrates a hybrid site comprising two CpG-SNP sites and FIG. 9B illustrates an indel site 910, according to a first set of example results.
Figure 9B:
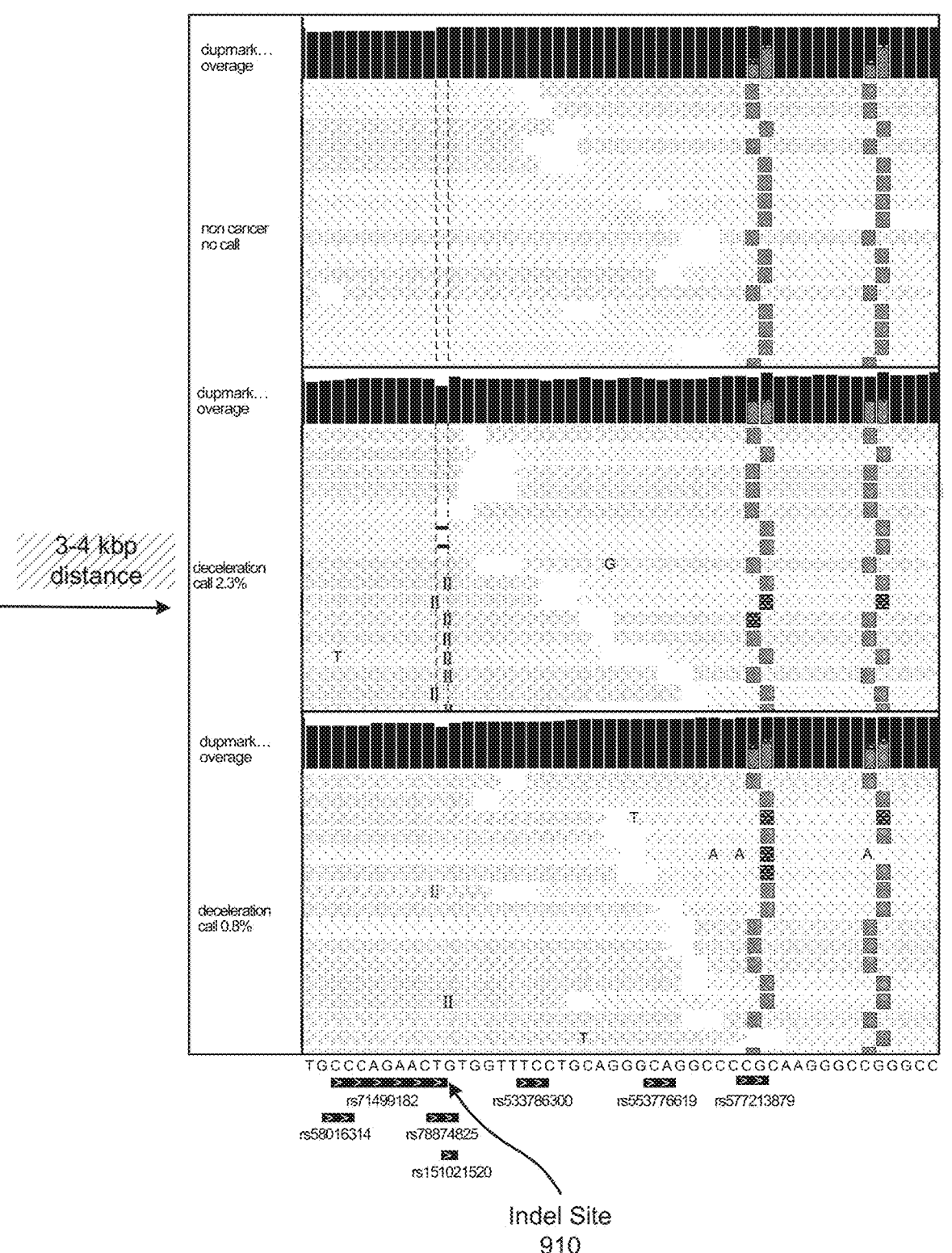
Figure 9C:
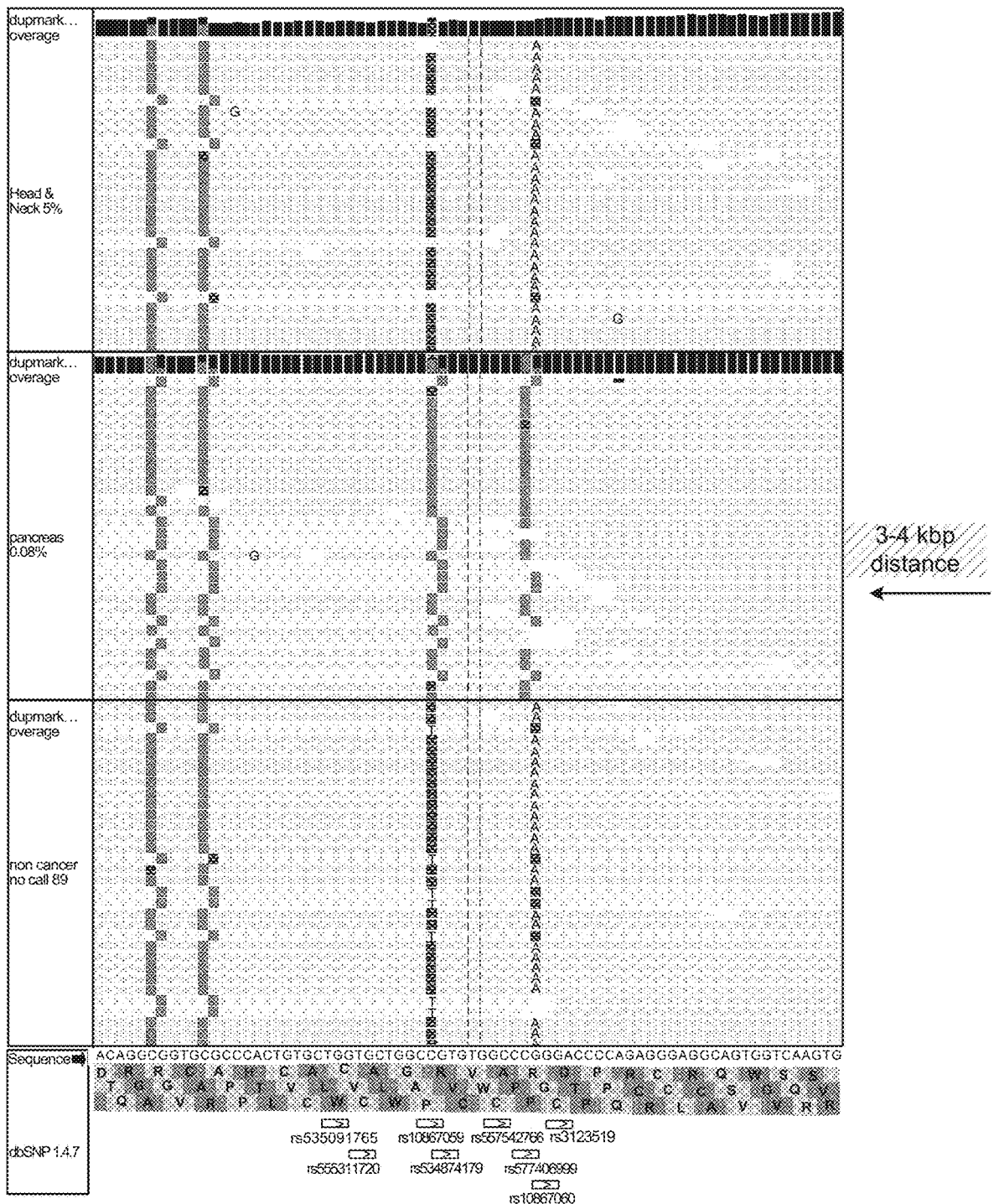
FIG. 9C further illustrates a hybrid site comprising two CpG-SNP sites and FIG. 9D illustrates the indel site 910, according to a second set of example results.
Figure 9D:
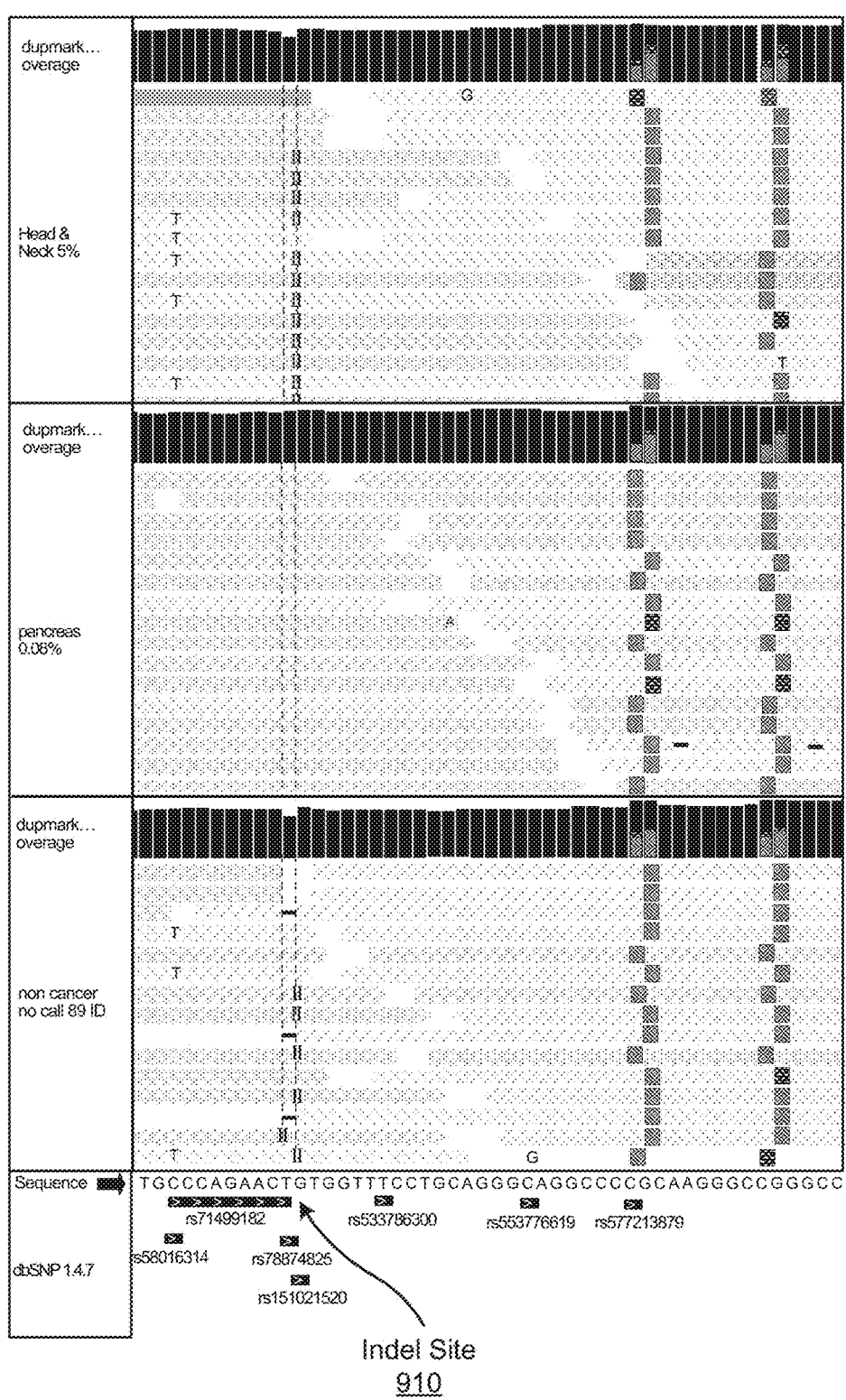

FIG. 9A further illustrates a hybrid site comprising two CpG-SNP sites and FIG. 9B illustrates an indel site 910, according to a first set of example results. FIG. 9C further illustrates a hybrid site comprising two CpG-SNP sites and FIG. 9D illustrates the indel site 910, according to a second set of example results. The hybrid site comprises the two CpG-SNP sites from FIG. 8 with an additional indel site 910 that is approximately 3-4 kilobasepairs (kbp) from the two CpG-SNP sites. Moreover, this insertion sequence creates a new CpG site. The reference sequence to the left and right of this insertion are T and G, so we get T<insertion>G=T<GCCCAGAAC>G (SEQ ID NO. 3) creating the underlined CpG when there is an insertion. The last "C" is methylated also reflecting that the neighboring G next to it is unconverted on the reverse strand.

Figure 9E:
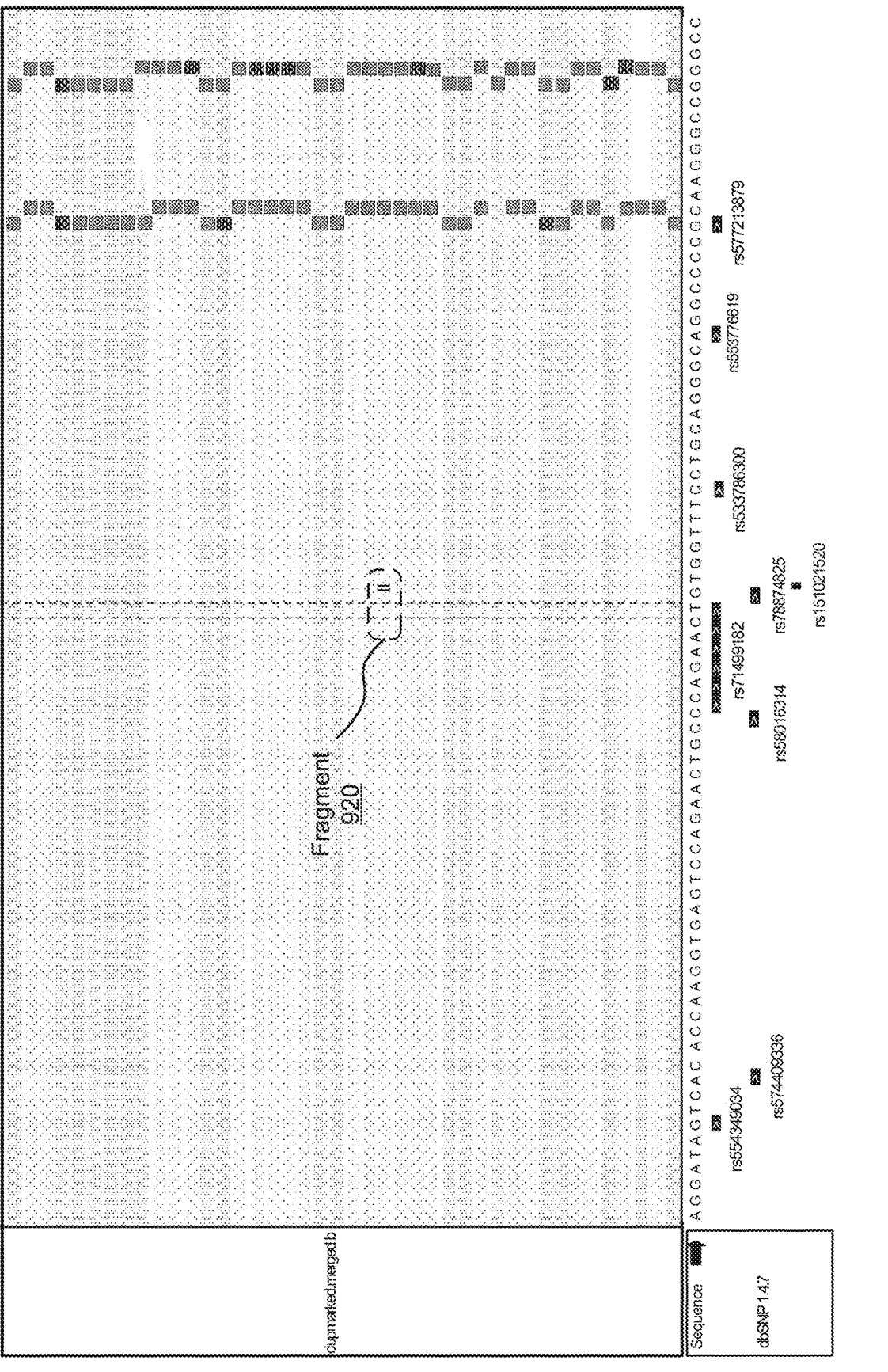
FIG. 9E illustrates contamination detection utilizing the hybrid site as a double CpG-SNP & indel site of FIGS. 9A-9D, according to example results.

FIG. 9E illustrates contamination detection utilizing the hybrid site as a double CpG-SNP & indel site of FIGS.

9A-9D, according to example results. The sequence reads for cfDNA fragments are shown for the same sample as FIG. 8B. In the sample, a large majority of the sequence reads show absence of the indel site. Fragment 920 shows presence of the insertion sequence. The analytics system may determine or call the fragment 920 to be a contamination fragment for having a different haplotype (presence of insertion sequence) compared to the homozygous haplotype (absence of the insertion sequence).

VI. Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein as being performed by the analytics system may be performed or implemented with one or more hardware or software modules of the apparatus, alone or in combination with other computing devices. In one embodiment, a software module is implemented with a computer program product comprising a computer-readable medium containing computer program code, which can be executed by a computer processor for performing any or all of the steps, operations, or processes described.

---

What is claimed:

1. A method for predicting a presence of cancer in a test sample, the method comprising:

i) obtaining the test sample comprising a plurality of cell-free DNA (cfDNA) fragments, the test sample collected from an individual;

ii) sequencing the cfDNA fragments with a plurality of probes designed to target a plurality of genetic markers yielding a plurality of sequence reads, the plurality of genetic markers including a plurality of CpG single nucleotide polymorphism (CpG-SNP) contamination markers for identifying any foreign fragments in the test sample belonging not to the individual associated with the test sample, wherein at least one of the plurality of CpG-SNP contamination markers comprises:

(a) an additive CpG-SNP site, wherein the SNP at the first CpG-SNP contamination marker creates a new CpG site, and wherein the first CpG-SNP contamination marker is one of: a thymine-cytosine polymorphism in a thymine-guanine dinucleotide, an adenine-cytosine polymorphism in an adenine-guanine dinucleotide, a guanine-cytosine polymorphism in a guanine-guanine dinucleotide, a thymine-guanine polymorphism in a cytosine-thymine dinucleotide, an adenine-guanine polymorphism in a cytosine-adenine dinucleotide, and a cytosine-guanine polymorphism in a cytosine-cytosine dinucleotide; or (b) a subtractive CpG-SNP site, wherein the SNP at the first CpG-SNP contamination marker removes a pre-existing CpG site, and wherein the first CpG-SNP contamination marker is one of: a cytosine-thymine polymorphism in a cytosine-guanine dinucleotide; a cytosine-adenine polymorphism in a cytosine-guanine dinucleotide; a cytosine-guanine polymorphism in a cytosine-guanine dinucleotide; a guanine-thymine polymorphism in a cytosine-guanine dinucleotide; a guanine-adenine polymorphism in a cytosine-guanine dinucleotide; and a guanine-cytosine polymorphism in a cytosine-guanine dinucleotide;

iii) identifying, based on the sequence reads, one or more CpG-SNP contamination markers from the plurality of CpG-SNP contamination markers for which the test sample has a homozygous haplotype;

iv) for each of the identified one or more CpG-SNP contamination markers for which the test sample has a homozygous haplotype, determining whether the sequence reads for the cfDNA fragments have a different haplotype at the identified CpG-SNP contamination marker than the homozygous haplotype of the test sample, wherein cfDNA fragments having a different haplotype at the identified CpG-SNP contamination marker than the homozygous haplotype of the test sample are labeled as contamination cfDNA fragments originating from another source that is not the individual;

v) determining if the test sample is contaminated based on a number of contamination cfDNA fragments being below a threshold; and vi) in response to determining that the test sample is contaminated, excluding the sample from further analysis;

vii) in response to determining that the test sample is not contaminated, applying a classification model to the sequence reads for the cfDNA fragments excluding any sequence reads associated with contamination cfDNA fragments and outputting a cancer prediction for the test sample based on the sequence reads for the cfDNA fragments.

2. The method of claim 1, wherein applying the classification model comprises: generating a test feature vector based on the sequence reads excluding any sequence reads associated with contamination cfDNA fragments; inputting the test feature vector into the classification model; and generating a cancer prediction for the test sample.

3. The method of claim 1, wherein a given CpG-SNP contamination marker has a population methylation frequency above a threshold frequency, and wherein the threshold frequency is selected from the range of 70%-100%.

4. The method of claim 1, wherein each CpG-SNP contamination marker has population haplotype frequencies within the range of 45%-55%.

5. The method of claim 1, wherein the haplotypes of each CpG-SNP contamination marker are in Hardy-Weinberg equilibrium.

6. The method of claim 1, wherein a given CpG-SNP contamination marker further comprises a second SNP affecting a second CpG site.

7. The method of claim 6, wherein the second CpG site and the first CpG site of the given CpG-SNP contamination marker are within a threshold distance, and wherein the threshold distance is selected from the range of 8 bp to 30 bp.

8. The method of claim 6, wherein: the first SNP removes the first CpG site and the second SNP removes the second CpG site, the first SNP removes the first CpG site and the second SNP creates the second CpG site, or the first SNP creates the first CpG site and the second SNP creates the second CpG site.

9. The method of claim 6, wherein the given CpG SNP marker has population haplotype frequencies within the range of 45%-55%.

10. The method of claim 6, wherein the haplotypes of the given CpG SNP marker are in Hardy-Weinberg equilibrium.

11. The method of claim 6, wherein the given SNP CpG marker further comprises an insertion or a deletion (indel) sequence within a threshold distance from the first CpG site and the second CpG site, and wherein the threshold distance is selected from 100 bp to 5 kbp.

12. The method of claim 11, wherein the insertion indel sequence is of a threshold length, and wherein the threshold length is selected from 5 bp to 30 bp.

13. The method of claim 12, wherein the insertion indel sequence affects a third CpG site.

14. The method of claim 1, wherein each contamination marker includes a probe designed to target each haplotype of the contamination marker.

15. The method of claim 1, wherein the cancer prediction is a binary prediction between cancer and non-cancer.

16. The method of claim 1, further comprising: filtering, after said obtaining, the cfDNA fragments of the test sample to generate a set of anomalous cfDNA fragments, wherein said filtering comprises removing cfDNA fragments having below a threshold p-value with respect to other fragments.

17. A system for predicting a presence of cancer in a test sample comprising:

a sequencing device configured to: i) load a test sample comprising a plurality of cell-free DNA (cfDNA) fragments, the test sample collected from an individual; ii) sequence the cfDNA fragments with a plurality of probes designed to target a plurality of genetic markers yielding a plurality of sequence reads, the plurality of genetic markers including a plurality of CpG single nucleotide polymorphism (CpG-SNP) contamination markers for identifying any foreign fragments in the test sample belonging not to the individual associated with the test sample, wherein at least one of the plurality of CpG-SNP contamination markers comprises:

(a) an additive CpG-SNP site, wherein the SNP at the first CpG-SNP contamination marker creates a new CpG site, and wherein the first CpG-SNP contamination marker is one of: a thymine-cytosine polymorphism in a thymine-guanine dinucleotide, an adenine-cytosine polymorphism in an adenine-guanine dinucleotide, a guanine-cytosine polymorphism in a guanine-guanine dinucleotide, a thymine-guanine polymorphism in a cytosine-thymine dinucleotide, an adenine-guanine polymorphism in a cytosine-adenine dinucleotide, and a cytosine-guanine polymorphism in a cytosine-cytosine dinucleotide; or (b) a subtractive CpG-SNP site, wherein the SNP at the first CpG-SNP contamination marker removes a pre-existing CpG site, and wherein the first CpG-SNP contamination marker is one of: a cytosine-thymine polymorphism in a cytosine-guanine dinucleotide; a cytosine-adenine polymorphism in a cytosine-guanine dinucleotide; a cytosine-guanine polymorphism in a cytosine-guanine dinucleotide; a guanine-thymine polymorphism in a cytosine-guanine dinucleotide; a guanine-adenine polymorphism in a cytosine-guanine dinucleotide; and a guanine-cytosine polymorphism in a cytosine-guanine dinucleotide;

a computer processor and a non-transitory computer-readable storing instructions that, when executed by the computer processor, cause the computer processor to perform operations comprising:

iii) identifying, based on the sequence reads, one or more CpG-SNP contamination markers from the plurality of CpG-SNP contamination markers for which the test sample has a homozygous haplotype;

iv) for each of the identified one or more CpG-SNP contamination markers for which the test sample has a homozygous haplotype, determining whether the sequence reads for the cfDNA fragments have a different haplotype at the identified CpG-SNP contamination marker than the homozygous haplotype of the test sample, wherein cfDNA fragments having a different haplotype at the identified CpG-SNP contamination marker than the homozygous haplotype of the test sample are labeled as contamination cfDNA fragments originating from another source that is not the individual;

v) determining if the test sample is contaminated based on a number of contamination cfDNA fragments being below a threshold; and vi) in response to determining that the test sample is contaminated, excluding the sample from further analysis;

vii) in response to determining that the test sample is not contaminated, applying a classification model to the sequence reads for the cfDNA fragments excluding any sequence reads associated with contamination cfDNA fragments and outputting a cancer prediction for the test sample based on the sequence reads for the cfDNA fragments.

18. The method of claim 1, wherein sequencing the cfDNA fragments yielding the plurality of sequence reads comprises: treating the cfDNA fragments to convert any unmethylated cytosines to uracils; and sequencing the treated cfDNA fragments to identify any uracils in the treated cfDNA fragments indicating unmethylation at a CpG site and to identify any unconverted cytosines in the treated cfDNA fragments indicating methylation at a CpG site.

* * * * *